(12) United States Patent
Stoltenburg et al.

(10) Patent No.: US 9,353,421 B2
(45) Date of Patent: May 31, 2016

(54) APTAMERS THAT ARE SPECIFIC FOR IMMUNOGLOBULIN-BINDING CELL WALL PROTEINS

(75) Inventors: Regina Stoltenburg, Leipzig (DE); Beate Strehlitz, Leipzig (DE)

(73) Assignee: Helmholtz-Zentrum für Umweltforschung GmbH-UFZ, Leipzig (DE)

( * ) Notice: Subject to any disclaimer, the term of this patent is extended or adjusted under 35 U.S.C. 154(b) by 132 days.

(21) Appl. No.: 14/009,088

(22) PCT Filed: Mar. 29, 2012

(86) PCT No.: PCT/EP2012/055655
§ 371 (c)(1),
(2), (4) Date: Jan. 24, 2014

(87) PCT Pub. No.: WO2012/130951
PCT Pub. Date: Oct. 4, 2012

(65) Prior Publication Data
US 2014/0141446 A1    May 22, 2014

(30) Foreign Application Priority Data
Mar. 31, 2011 (DE) .......................... 10 2011 066 610

(51) Int. Cl.
| | | |
|---|---|---|
| *A61K 31/70* | (2006.01) | |
| *C07H 21/02* | (2006.01) | |
| *C07H 21/04* | (2006.01) | |
| *C12Q 1/68* | (2006.01) | |
| *C12N 15/115* | (2010.01) | |
| *A61K 31/711* | (2006.01) | |

(52) U.S. Cl.
CPC .............. *C12Q 1/689* (2013.01); *C12N 15/115* (2013.01); *A61K 31/711* (2013.01); *C12N 2310/16* (2013.01)

(58) Field of Classification Search
None
See application file for complete search history.

(56) References Cited

U.S. PATENT DOCUMENTS

| | | | |
|---|---|---|---|
| 5,270,163 A | 12/1993 | Gold et al. | |
| 5,567,588 A | 10/1996 | Gold et al. | |
| 2009/0203028 A1 | 8/2009 | Yamamoto et al. | |

FOREIGN PATENT DOCUMENTS

| | | |
|---|---|---|
| JP | 2010158238 | 7/2010 |
| KR | 2009-0032285 | 4/2009 |
| KR | 2010-0060213 | 6/2010 |
| KR | 2010-0083970 | 7/2010 |
| KR | 2010-0130092 | 12/2010 |
| WO | 2005/113817 | 12/2005 |

OTHER PUBLICATIONS

Bannantine et al., "Development and Characterization of Monoclonal Antibodies and Aptamers against Major Antigens of *Mycobacterium avium* subsp. *paratuberculosis*", Clinical and Vaccine Immunology (2007), vol. 14, No. 5, pp. 518-526.
Bruno et al., "In Vitro Antibacterial Effects of Antilipopolysaccharide DNA Aptanner-C1qrs Complexes", Folia Microbiol. (2008), vol. 53, No. 4, pp. 295-302.
Cao et al., "Combining use of a panel of ssDNA aptamers in the detection of *Staphylococcus aureus*", Nucleic Acids Research (2009), vol. 37, No. 14, pp. 4621-4628.
Cho et al., "Applications of Aptamers as Sensors", Annual Review of Analytical Chemistry (2009), vol. 2, pp. 241-264.
Ciesiolka et al., "Affinity Selection-Amplification from Randomized Ribooligunucleotide Pools", Methods in Enzymology (1996), vol. 267, pp. 315-335.
Conrad et al., "In Vitro Selection of Nucleic Acid Aptamers That Bind Proteins", Methods in Enzymology (1996), vol. 267, pp. 336-383.
Ellington et al., "In vitro selection of RNA molecules that bind specific ligands", Nature (1990), vol. 346, pp. 818-822.
Fitzwater et al., "A SELEX Primer", Methods in Enzymology (1996), vol. 267, pp. 275-301.
Fowler et al., "Aptamers and Their Potential as Recognition Elements for the Detection of Bacteria", Principles of Bacterial Detection: Biosensors, Recognition Receptors and Microsystems (2008), pp. 689-714.
Gnanam et al., "Development of aptamers specific for potential diagnostic targets in Burkholderia pseudomallei", Transactions of the Royal Society of Tropical Medicine and Hygiene (2008), vol. 102, No. S1, pp. S55-S57.
Hamula et al., "Selection of Aptamers against Live Bacterial Cells", Anal. Chem. (2008), vol. 80, No. 20, pp. 7812-7819.
Joshi et al., "Selection, characterization, and application of DNA aptamers for the capture and detection of *Salmonella enterica* serovars", Molecular and Cellular Probes (2009), vol. 23, pp. 20-28.
Kim et al., "Molecular Recognition and Specific Interactions for Biosensing Applications", Sensors (2008), vol. 8, pp. 6605-6641.
Kulbachinskiy, A.V., "Methods for Selection of Aptamers to Protein Targets", Biochemistry (Moscow) (2007), vol. 72, No. 13, pp. 1505-1518.

(Continued)

*Primary Examiner* — Sean McGarry
(74) *Attorney, Agent, or Firm* — Hunton & Williams LLP

(57) ABSTRACT

The invention relates to an aptamer that binds to protein A, G or L, protein A-, G- or L-containing substances, and also to protein A-, G- or L-containing microorganisms, in particular *Staphylococcus aureus, Streptococcus* or *Peptostreptococcus*, methods for detection and enrichment of protein A, G or L, protein A-, G- or L-containing substances or protein A-, G- or L-containing microorganisms in which the aptamer is used, and also a kit, a biosensor, a lateral flow assay device and a measuring instrument which contain such an aptamer and can be used in said methods.

44 Claims, 9 Drawing Sheets

(56) References Cited

OTHER PUBLICATIONS

Mok et al., "Recent Progress in Nucleic Acid Aptamer-Based Biosensors and Bioassays", Sensors (2008), vol. 8, pp. 7050-7084.

Pan et al., "Aptamers That Preferentially Bind Type IVB Pili and Inhibit Human Monocytic-Cell Invasion by *Salmonella enterica* Serovar Typhi", Antimicrobial Agents and Chemotherapy (2005), vol. 49, No. 10, pp. 4052-4060.

Purschke et al., "A DNA Spiegelmer to staphylococcal enterotoxin B", Nucleic Acids Research (2003), vol. 31, No. 12, pp. 3027-3032.

Song et al., "Aptamer-based biosensors", Trends in Analytical Chemistry (2008), vol. 27, No. 2, pp. 108-117.

Stoltenburg et al., "FluMag-SELEX as an advantageous method for DNA aptamer selection", Anal. Bioanal. Chem. (2005), vol. 383, pp. 83-91.

Tuerk et al., "Systematic Evolution of Ligands by Exponential Enrichment: RNA Ligands to Bacteriophage T4 DNA Polymerase", Science (1990), vol. 249, pp. 505-510.

Vivekananda et al., "Anti-Francisella tularensis DNA aptamers detect tularemia antigen from different subspecies by Aptamer-Linked Immobilized Sorbent Assay", Laboratory Investigation (2006), vol. 86, pp. 610-618.

Zuker, M., "Mfold web server for nucleic acid folding and hybridization prediction", Nucleic Acids Research (2003), vol. 31, No. 13, pp. 3406-3415.

SEQUENCE LISTING

<160> NUMBER OF SEQ ID NOS: 71

<210> SEQ ID NO 1
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 1

```
ataccagctt attcaattag caacatgagg gggatagagg gggtgggttc tctcggctac    60
aatcgtaatc agttag                                                   76

<210> SEQ ID NO 2
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 2
ataccagctt attcaattag caacatgagg gggatagagg gggtgggttc tctcgrctac    60
aatcgtaatc agttag                                                   76

<210> SEQ ID NO 3
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 3
ataccagctt attcaattag caacatgagg gggataaagg gggtgggttc tctcggctac    60
aatcgtaatc agttag                                                   76

<210> SEQ ID NO 4
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 4
ataccagctt attcaattag caacatgagg gggatggagg gggtgggttc tcttggctac    60
aatcgtaatc agttag                                                   76

<210> SEQ ID NO 5
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 5
ataccagctt attcaattcc ccaacgagtc gatatgtagc ccacactctg attcgtccac    60
aatcgtaatc agttag                                                   76

<210> SEQ ID NO 6
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 6
ataccagctt attcaattgc acaacgagtc gatatgtagc ccacactctg attcgtccac    60
aatcgtaatc agttag                                                   76

<210> SEQ ID NO 7
<211> LENGTH: 76
<212> TYPE: DNA
<213> ORGANISM: Artificial Sequence
```

```
<220> FEATURE:
<223> OTHER INFORMATION: DNA-Aptamer

<400> SEQUENCE: 7
ataccagctt attcaattcc ccaacgagtc gatatgtagc ccacattctg attcgtccac    60
aatcgtaatc agttag                                                    76

<210> SEQ ID NO 8
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 8
ataccagctt attcaattac ccaacgagtc gatatgtagc ccacactctg attcgtccac    60
aatcgtaatc agttag                                                    76

<210> SEQ ID NO 9
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 9
ataccagctt attcaattac cgatcactag ccgactaatt ggtttccgat cgcagtccac    60
aatcgtaatc agttag                                                    76

<210> SEQ ID NO 10
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 10
ataccagctt attcaattac cgatcactag ccgactaatt ggtttccgat cgcagttcac    60
aatcgtaatc agttag                                                    76

<210> SEQ ID NO 11
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 11
ataccagctt attcaattcc acaaccgaac tcgtaagacg tatgtagccg ccaactgtac    60
aatcgtaatc agttag                                                    76

<210> SEQ ID NO 12
<211> LENGTH: 75
<212> TYPE: DNA
<213> ORGANISM: Artificial Sequence
<220> FEATURE:
<223> OTHER INFORMATION: DNA-Aptamer

<400> SEQUENCE: 12
ataccagctt attcaattcc caaccgaact cgtaagacgt atgtagccgc caactgtaca    60
atcgtaatca gttag                                                     75
```

```
<210> SEQ ID NO 13
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 13
ataccagctt attcaattgc agtactgatg agtgtagccg tatgattatc gtttgtggac    60
aatcgtaatc agttag                                                   76

<210> SEQ ID NO 14
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 14
ataccagctt attcaattgg agacgacaaa ctattacgta ctacggcatg cacttggtac    60
aatcgtaatc agttag                                                   76

<210> SEQ ID NO 15
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 15
ataccagctt attcaattcg acaagtgggc attacgattc tagccctgat tatgttccac    60
aatcgtaatc agttag                                                   76

<210> SEQ ID NO 16
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 16
ataccagctt attcaattac gcattggagc ccgaaactga ttcattgagc ctacctgtac    60
aatcgtaatc agttag                                                   76

<210> SEQ ID NO 17
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 17
ataccagctt attcaattac gaccgtagac gacttacact gatgttgcgc atttctgtac    60
aatcgtaatc agttag                                                   76

<210> SEQ ID NO 18
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 18
```
ataccagctt attcaattcg atgacgactg tagccgcaat acgcccctgt tacgttgtac    60
aatcgtaatc agttag                                                    76

<210> SEQ ID NO 19
<211> LENGTH: 77
<212> TYPE: DNA
<213> ORGANISM: Artificial Sequence
<220> FEATURE:
<223> OTHER INFORMATION: DNA-Aptamer

<400> SEQUENCE: 19
ataccagctt attcaattgg acgccgacta actttacgtg gttctcctac cgcctaacca    60
caatcgtaat cagttag                                                   77

<210> SEQ ID NO 20
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 20
ataccagctt attcaattac gaaatgtagc cgatcctgat tactctctgt cagcttggac    60
aatcgtaatc agttag                                                    76

<210> SEQ ID NO 21
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 21
ataccagctt attcaattgg agtccgacta aatgatcttt gagagtgtct cacagtccac    60
aatcgtaatc agttag                                                    76

<210> SEQ ID NO 22
<211> LENGTH: 77
<212> TYPE: DNA
<213> ORGANISM: Artificial Sequence
<220> FEATURE:
<223> OTHER INFORMATION: DNA-Aptamer

<400> SEQUENCE: 22
ataccagctt attcaattgc agattacgcc ttgtagcccg cactgatctc gatatttgga    60
caatcgtaat cagttag                                                   77

<210> SEQ ID NO 23
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 23
ataccagctt attcaattac gaggtacgat tacagacgat cgaactgata cttgttggac    60
aatcgtaatc agttag                                                    76

<210> SEQ ID NO 24
<211> LENGTH: 76
<212> TYPE: DNA

```
<213> ORGANISM: Artificial Sequence
<220> FEATURE:
<223> OTHER INFORMATION: DNA-Aptamer

<400> SEQUENCE: 24
ataccagctt attcaattac gatcactgta gacggcgact gattaatcta cgtattggac    60
aatcgtaatc agttag                                                    76

<210> SEQ ID NO 25
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 25
ataccagctt attcaattgc aatggacccc aaagttggat tgtagccgct gctgttcgac    60
aatcgtaatc agttag                                                    76

<210> SEQ ID NO 26
<211> LENGTH: 77
<212> TYPE: DNA
<213> ORGANISM: Artificial Sequence
<220> FEATURE:
<223> OTHER INFORMATION: DNA-Aptamer

<400> SEQUENCE: 26
ataccagctt attcaattac ggcaacgagt gtagaccgac gctgattact gtctcatcga    60
caatcgtaat cagttag                                                   77

<210> SEQ ID NO 27
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 27
ataccagctt attcaattgc accaacccgc tgataggatg tagccgctaa ctccttccac    60
aatcgtaatc agttag                                                    76

<210> SEQ ID NO 28
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 28
ataccagctt attcaattgg agacgacgcc tggtttcgtt attgagtgtc tctctgccac    60
aatcgtaatc agttag                                                    76

<210> SEQ ID NO 29
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 29
ataccagctt attcaattgg agccgcaaat atcgtgatga atgtgtgagc cgatctacac    60
aatcgtaatc agttag                                                    76
```

<210> SEQ ID NO 30
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 30
ataccagctt attcaattac cccgatgtag ccgacgtgca cttgttatga ttaggaccac    60
aatcgtaatc agttag                                                   76

<210> SEQ ID NO 31
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 31
ataccagctt attcaattcc agaaccggcg attgtaaccg actaagtgtg catgatccac    60
aatcgtaatc agttag                                                   76

<210> SEQ ID NO 32
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 32
ataccagctt attcaattgc agccgactaa cctgatgagt gtggtcagtt tacgcttgac    60
aatcgtaatc agttag                                                   76

<210> SEQ ID NO 33
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 33
ataccagctt attcaattgg agacgacgcg gctgattatg ttagtctgta acgccaccac    60
aatcgtaatc agttag                                                   76

<210> SEQ ID NO 34
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 34
ataccagctt attcaattac gaacatggag ccgcactgat tactggtcca ccgcgtacac    60
aatcgtaatc agttag                                                   76

<210> SEQ ID NO 35
<211> LENGTH: 78
<212> TYPE: DNA
<213> ORGANISM: Artificial Sequence
<220> FEATURE:
<223> OTHER INFORMATION: DNA-Aptamer -continued

```
<400> SEQUENCE: 35
ataccagctt attcaattgt agccgaacac gaactgacac taattgccga tggcacctgc    60
acaatcgtaa tcagttag                                                  78

<210> SEQ ID NO 36
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 36
ataccagctt attcaattgg agccgaacaa ctgcttaccc tgcgtcttat tgtcccgtac    60
aatcgtaatc agttag                                                    76

<210> SEQ ID NO 37
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 37
ataccagctt attcaattgg agacgactag ctgcttacga tgactctgta ctgtaaccac    60
aatcgtaatc agttag                                                    76

<210> SEQ ID NO 38
<211> LENGTH: 77
<212> TYPE: DNA
<213> ORGANISM: Artificial Sequence
<220> FEATURE:
<223> OTHER INFORMATION: DNA-Aptamer

<400> SEQUENCE: 38
ataccagctt attcaattac gaacagtagc cgcataaact ctacagatat tctcgttgga    60
caatcgtaat cagttag                                                   77

<210> SEQ ID NO 39
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 39
ataccagctt attcaattac gatgtagtcc gactccaact gatgattgtt acgccgccac    60
aatcgtaatc agttag                                                    76

<210> SEQ ID NO 40
<211> LENGTH: 75
<212> TYPE: DNA
<213> ORGANISM: Artificial Sequence
<220> FEATURE:
<223> OTHER INFORMATION: DNA-Aptamer

<400> SEQUENCE: 40
ataccagctt attcaattgg acgccgacta acttacgatt gctagataac tgtttccaca    60
atcgtaatca gttag                                                     75

<210> SEQ ID NO 41
<211> LENGTH: 76
```

```
<212> TYPE: DNA
<213> ORGANISM: Artificial Sequence
<220> FEATURE:
<223> OTHER INFORMATION: DNA-Aptamer

<400> SEQUENCE: 41
ataccagctt attcaattac cgatttagac gatccataca gtctgattaa cgtgttgcac      60
aatcgtaatc agttag                                                     76

<210> SEQ ID NO 42
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 42
ataccagctt attcaattac gatgccagcc gaaactcaga ttacgttctt gaccgtggac      60
aatcgtaatc agttag                                                     76

<210> SEQ ID NO 43
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 43
ataccagctt attcaattac gatgtagccg ttccctttac gatgtgcacc gactaaccac      60
aatcgtaatc agttag                                                     76

<210> SEQ ID NO 44
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 44
ataccagctt attcaattgg gtacgagata gccgtctttc gatctgagtc cattggatac      60
aatcgtaatc agttag                                                     76

<210> SEQ ID NO 45
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 45
ataccagctt attcaattcc aactgcacga tgtagccgga cctctaatga ttacctgtac      60
aatcgtaatc agttag                                                     76

<210> SEQ ID NO 46
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 46
ataccagctt attcaattgt acgccgactg actgagaaat gtgcttgagt tcgcatcgac      60
```
aatcgtaatc agttag                                                          76

<210> SEQ ID NO 47
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 47
ataccagctt attcaattgg agccgaactg tctgagtagt gttgacattc ttctacgtac         60
aatcgtaatc agttag                                                          76

<210> SEQ ID NO 48
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 48
ataccagctt attcaattac cgagacgtgg aaccgattgt tgccgcactg attattccac         60
aatcgtaatc agttag                                                          76

<210> SEQ ID NO 49
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 49
ataccagctt attcaattgg agacgacccg aactgactat gtagaatgtg tccgacccac         60
aatcgtaatc agttag                                                          76

<210> SEQ ID NO 50
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 50
ataccagctt attcaattgt agacgacgaa ctgttatgac attttttctt gtcctcacac         60
aatcgtaatc agttag                                                          76

<210> SEQ ID NO 51
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 51
ataccagctt attcaattcc aatgatcgat tgttgccctg attgatggtt gttgtcgtac         60
aatcgtaatc agttag                                                          76

<210> SEQ ID NO 52
<211> LENGTH: 76
<212> TYPE: DNA
<213> ORGANISM: Artificial Sequence
<220> FEATURE:
<223> OTHER INFORMATION: DNA-Aptamer

```
<400> SEQUENCE: 52
ataccagctt attcaattgg acgccgacta acttaagcga tttggcccac tcatctcgac    60
aatcgtaatc agttag                                                   76

<210> SEQ ID NO 53
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 53
ataccagctt attcaattgg agacgctaac atgatgctac gaaggtgtga atcggtgcac    60
aatcgtaatc agttag                                                   76

<210> SEQ ID NO 54
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 54
ataccagctt attcaattgg gcaccacggg agtcggccac atttggagtt gttttttgcac   60 aatcgtaatc agttag                                                   76

<210> SEQ ID NO 55
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 55
ataccagctt attcaattcg agtgtggccg ccaactgagc ttgttagtgt cctcttgtac    60
aatcgtaatc agttag                                                   76

<210> SEQ ID NO 56
<211> LENGTH: 74
<212> TYPE: DNA
<213> ORGANISM: Artificial Sequence
<220> FEATURE:
<223> OTHER INFORMATION: DNA-Aptamer

<400> SEQUENCE: 56
ataccagctt attcaattgt agacgacgac tgtacgttga cctgctaacc acttctggac    60
aatcgtaatc agtt                                                     74

<210> SEQ ID NO 57
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 57
ataccagctt attcaattgc accagtggaa agattgtagc cgttcctcct gattatgcac    60
aatcgtaatc agttag                                                   76

<210> SEQ ID NO 58
```

```
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 58
ataccagctt attcaattgc acggtgggag attgtagccc ctcttttttt ttgcctgtac      60
aatcgtaatc agttag                                                     76

<210> SEQ ID NO 59
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 59
ataccagctt attcaattgt agacgaccac ctgattaact ttggccgggc cctttgtac       60 aatcgtaatc agttag                                                     76

<210> SEQ ID NO 60
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 60
ataccagctt attcaattac gatccttgta gcccagcgca ctgatcacgc ttgtgaccac      60
aatcgtaatc agttag                                                     76

<210> SEQ ID NO 61
<211> LENGTH: 76
<212> TYPE: DNA
<213> ORGANISM: Artificial Sequence
<220> FEATURE:
<223> OTHER INFORMATION: DNA-Aptamer

<400> SEQUENCE: 61
ataccagctt attcaattgt agacgacgca atataatgat tagttggcac gaccctgcac      60
aatcgtaatc agttag                                                     76

<210> SEQ ID NO 62
<211> LENGTH: 76
<212> TYPE: DNA
<213> ORGANISM: Artificial Sequence
<220> FEATURE:
<223> OTHER INFORMATION: DNA-Aptamer: Zusammenfassung der Sequenzen der
      Gruppe 1 (SEQ ID NOs: 1-4)

<400> SEQUENCE: 62
ataccagctt attcaattag caacatgagg gggatrragg gggtgggttc tctygrctac      60
aatcgtaatc agttag                                                     76

<210> SEQ ID NO 63
<211> LENGTH: 76
<212> TYPE: DNA
<213> ORGANISM: Artificial Sequence
<220> FEATURE:
<223> OTHER INFORMATION: DNA-Aptamer: Zusammenfassung der Sequenzen der
      Gruppe 2 (SEQ ID NOs: 5-8)

<400> SEQUENCE: 63
```
ataccagctt attcaattvc mcaacgagtc gatatgtagc ccacaytctg attcgtccac    60
aatcgtaatc agttag                                                    76

<210> SEQ ID NO 64
<211> LENGTH: 76
<212> TYPE: DNA
<213> ORGANISM: Artificial Sequence
<220> FEATURE:
<223> OTHER INFORMATION: DNA-Aptamer: Zusammenfassung der Sequenzen der
      Gruppe 3 (SEQ ID NOs: 9-10)

<400> SEQUENCE: 64
ataccagctt attcaattac cgatcactag ccgactaatt ggtttccgat cgcagtycac    60
aatcgtaatc agttag                                                    76

<210> SEQ ID NO 65
<211> LENGTH: 76
<212> TYPE: DNA
<213> ORGANISM: Artificial Sequence
<220> FEATURE:
<223> OTHER INFORMATION: DNA-Aptamer: Zusammenfassung der Sequenzen der
      Gruppe 4 (SEQ ID NOs: 11-12)
<220> FEATURE:
<221> NAME/KEY: mutation
<222> LOCATION: (21)..(21)
<223> OTHER INFORMATION: deletion

<400> SEQUENCE: 65
ataccagctt attcaattcc acaaccgaac tcgtaagacg tatgtagccg ccaactgtac    60
aatcgtaatc agttag                                                    76

<210> SEQ ID NO 66
<211> LENGTH: 18
<212> TYPE: DNA
<213> ORGANISM: Artificial Sequence
<220> FEATURE:
<223> OTHER INFORMATION: Sense-Primer

<400> SEQUENCE: 66
ataccagctt attcaatt                                                  18

<210> SEQ ID NO 67
<211> LENGTH: 18
<212> TYPE: DNA
<213> ORGANISM: Artificial Sequence
<220> FEATURE:
<223> OTHER INFORMATION: Bindungsregion fur Antisense-Primer

<400> SEQUENCE: 67
acaatcgtaa tcagttag                                                  18

<210> SEQ ID NO 68
<211> LENGTH: 18
<212> TYPE: DNA
<213> ORGANISM: Artificial Sequence
<220> FEATURE:
<223> OTHER INFORMATION: Antisense-Primer

<400> SEQUENCE: 68
ctaactgatt acgattgt                                                  18

<210> SEQ ID NO 69
<211> LENGTH: 58
<212> TYPE: DNA

```
<213> ORGANISM: Artificial Sequence
<220> FEATURE:
<223> OTHER INFORMATION: DNA-Aptamer, trunkierte Variante von Aptamer
      PA#2/8

<400> SEQUENCE: 69
agcaacatga gggggataga gggggtgggt tctctcggct acaatcgtaa tcagttag         58

<210> SEQ ID NO 70
<211> LENGTH: 58
<212> TYPE: DNA
<213> ORGANISM: Artificial Sequence
<220> FEATURE:
<223> OTHER INFORMATION: DNA-Aptamer, trunkierte Variante von Aptamer
      PA#2/8

<400> SEQUENCE: 70
ataccagctt attcaattag caacatgagg gggatagagg gggtgggttc tctcggct         58

<210> SEQ ID NO 71
<211> LENGTH: 40
<212> TYPE: DNA
<213> ORGANISM: Artificial Sequence
<220> FEATURE:
<223> OTHER INFORMATION: DNA-Aptamer, trunkierte Variante von Aptamer
      PA#2/8

<400> SEQUENCE: 71
agcaacatga gggggataga gggggtgggt tctctcggct                             40
```

APTAMERS THAT ARE SPECIFIC FOR IMMUNOGLOBULIN-BINDING CELL WALL PROTEINS

CROSS-REFERENCE TO RELATED APPLICATIONS

This application is the U.S. National Phase of International Patent Application No. PCT/EP2012/055655, filed Mar. 29, 2012, which claims priority to DE 10 2011 006 610.1, filed Mar. 31, 2011, the contents of each are hereby incorporated by reference in their entireties.

BACKGROUND OF THE INVENTION

The present invention relates to an aptamer which binds to protein A, G or L, substances comprising protein A, G or L or microorganisms comprising protein A, G or L, in particular *Staphylococcus aureus, Streptococcus* or *Peptostreptococcus*, uses of the aptamer and methods for the detection and enrichment of protein A, G or L, substances comprising protein A, G or L or microorganisms comprising protein A, G or L in which the aptamer is employed.

*Staphylococcus aureus* is a spherical, Gram-positive, pathogenic bacterium. *S. aureus* occurs almost everywhere in nature, including on the skin and in the upper respiratory passages of 25 to 30% of all humans. Antibiotic-resistant forms and especially multiresistant forms are particularly hazardous. These occur to an increased extent in hospitals, care homes, and also in sewerage sludge. Resistant germs of the strain are also found in foodstuffs of animal origin. The germ can also enter into drinking water. Frequent diseases which are to be attributed to *S. aureus* are sepsis, skin and wound infections, pneumonias, abscesses, furuncles, endocarditis, osteomyelitis, food poisonings by *S. aureus* exotoxins and mastitis in cattle.

The detection of *S. aureus* has hitherto been carried out by means of cultivation or immunological and molecular biology methods (antibody assays, PCR-based methods). The methods are either time-consuming or expensive. The object of the present invention was therefore to provide specific substances which render possible a rapid, simple and reliable detection of *S. aureus*.

The object is achieved with an aptamer which binds to immunoglobulin-binding cell wall proteins, to substances which comprise an immunoglobulin-binding cell wall protein and to microorganisms which comprise an immunoglobulin-binding cell wall protein, wherein the immunoglobulin-binding cell wall protein is chosen from the group including or consisting of protein A, G or L.

In the context of the above paragraph, the term "including" means that the aptamer can also bind to further immunoglobulin-binding cell wall proteins, or to substances or microorganisms which comprise an immunoglobulin-binding cell wall protein other than the proteins A, G or L mentioned.

SUMMARY OF THE INVENTION

An aptamer which binds to protein A, G or L, substances comprising protein A, G or L and microorganisms comprising protein A, G or L, in particular *Staphylococcus aureus, Streptococcus* or *Peptostreptococcus* is thus provided. In particular, the aptamer according to the invention is specific for protein A, G or L. The aptamer according to the invention is a nucleic acid aptamer, in particular a single-stranded DNA (ssDNA) aptamer or an RNA aptamer.

That the aptamer binds to a substance which comprises an immunoglobulin-binding cell wall protein or to a microorganism which comprises an immunoglobulin-binding cell wall protein means in particular that the aptamer binds to the cell wall protein which is present in the substance or which is part of the microorganism. In other words, the aptamer binds to the cell wall protein itself, i.e. directly to the cell wall protein. Preferably, the aptamer binds only to the cell wall protein present in the substance or in/on the microorganism and not to another site of the substance or microorganism.

DETAILED DESCRIPTION OF THE INVENTION

Figure 1:
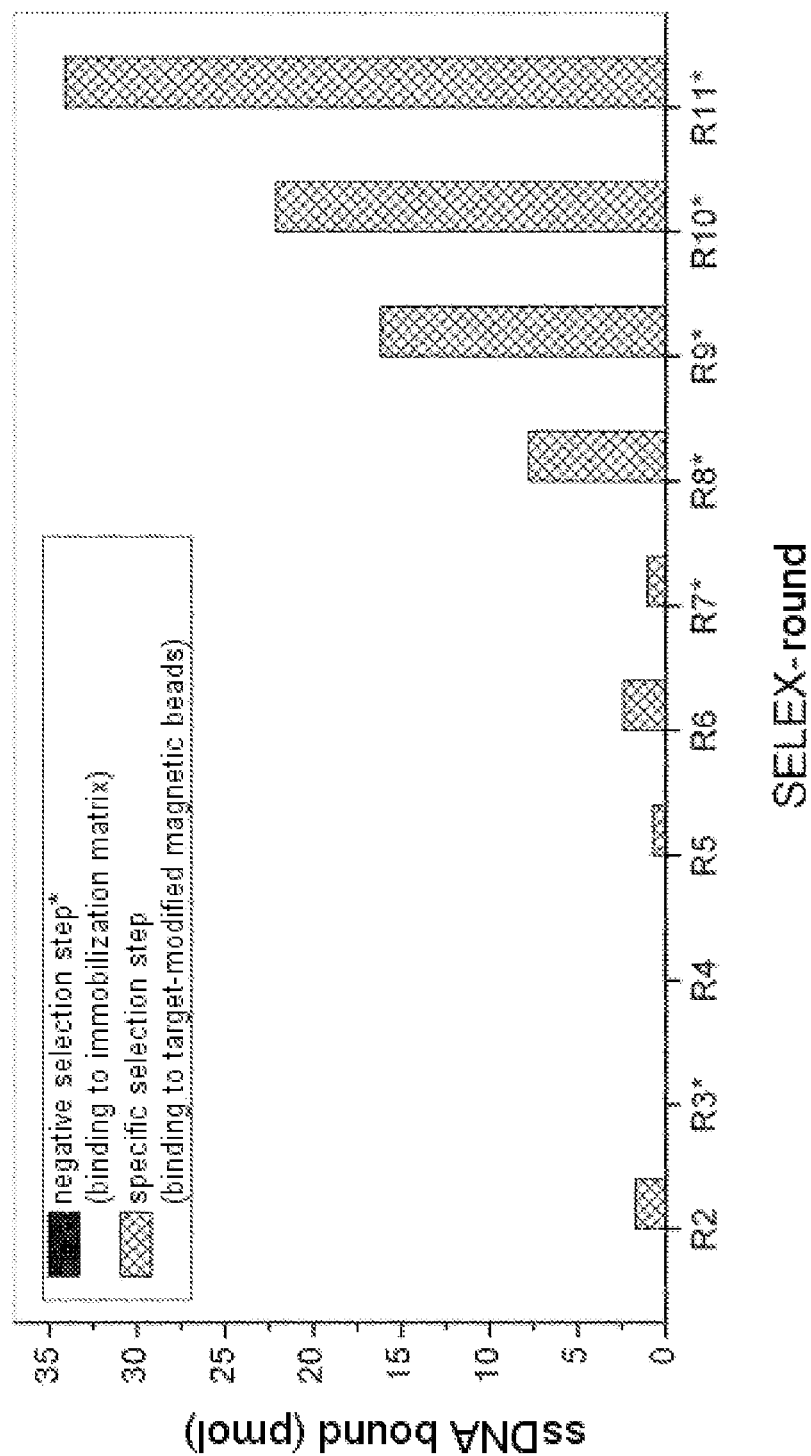
FIG. 1 shows the amount of oligonucleotides binding to target-modified magnetic beads in various SELEX rounds.

In the prior art the general term "aptamers" describes short single-stranded nucleic acid oligomers, also called oligonucleotides, which can bind specifically to a target structure or a target molecule, also called a target, for example to a protein, to low molecular weight compounds, such as organic substances, amino acids and antibiotics, nucleic acids, virus particles or (micro)organisms. The aptamer-target binding takes place, for example, via the structure compatibility, so-called "stacking interactions" in aromatic ring structures (stacking forces by electron interaction with adjacent bases), electrostatic interactions (e.g. van der Waals, ionic, dipole forces) and hydrogen bridge bonds.

Aptamers having a peptide structure are also known, wherein the present invention relates exclusively to nucleic acid aptamers. The term "aptamers" in the following thus means nucleic acid aptamers. In the case of nucleic acid aptamers, a distinction is made, for example, between DNA aptamers formed from single-stranded DNA (ssDNA), and RNA aptamers. Aptamers are distinguished by the formation of a specific three-dimensional structure, which depends on the nucleic acid sequence. This structure enables aptamers to bind target structures with an accurate fit analogously to an antigen-antibody binding. Under defined conditions a particular nucleic acid sequence of an aptamer can have a three-dimensional structure which is specific for a defined target structure (target). The three-dimensional structure of an aptamer arises inter alia as a result of intramolecular Watson and Crick base pairings and via Hoogsteen base pairings (quadruplex).

The statement that an aptamer according to the invention binds to protein A, G or L, a substance comprising protein A, G or L or a microorganism comprising protein A, G or L, or is specific for this, means that it binds to one or more targets which are chosen from protein A, G or L, a substance comprising protein A, G or L or a microorganism comprising protein A, G or L.

Protein A, protein G and protein L are bacterial cell wall proteins. They belong to a group of proteins which comprise recurring domains which can bind immunoglobulins.

Protein A is a protein which occurs in the cell wall of the bacterium *Staphylococcus aureus*. Protein A has a size of 40-60 kDa and is often used in biochemical research because of its ability to bind immunoglobulins via the Fc region thereof. Protein A binds various classes of immunoglobulins, in particular various IgG subclasses of various species. Examples of protein A representatives have the UniProt no. P38507, P02976, P99134, P0A015 (from the section: Swiss-Prot. of the UniProtKB=Protein knowledgebase).

Protein G is a protein which occurs in the cell wall of bacteria of the genus *Streptococcus*. Depending on the *Streptococcus* strain, it has a molecular weight of from about 58 to 65 kDa and has on the C terminus two or three homologous binding domains of high affinity for the Fc region of immunoglobulins, in particular of the IgG isotype. Furthermore, it also binds to albumin proteins via three homologous domains N-terminally to the IgG binding region. On the N terminus protein G has a further binding region (region E) for human alpha-2-globulin in the native conformation, also called the s form. Examples of protein G representatives have the UniProt (Universal Protein Database) no. P06654 and P19909.

Protein L is a protein which occurs in the cell wall of *Peptostreptococcus magnus*. Similarly to protein A and G, it is likewise capable of binding immunoglobulins, in particular immunoglobulins which comprise the light chains of the kappa type.

Due to their specificity for protein A, G or L, aptamers of the present invention are also specific for substances comprising protein A, G or L and microorganisms comprising protein A, G or L, in particular *Staphylococcus aureus*, *Streptococcus* or *Peptostreptococcus*. "Substances comprising protein A, G or L" are to be understood as meaning substances which are firmly bonded to protein A, G or L, for example by a covalent bond, hydrogen bridge bonds or a complex bond. Their specificity results in numerous possible uses of the aptamers according to the invention, which are explained further elsewhere in this description.

The aptamers according to the invention are also specific for protein A, protein G or protein L produced by recombinant methods, for example protein A, G or L produced by recombinant methods in *E. coli*.

Likewise, the terms protein A, protein G and protein L are also intended to include mutation forms of these proteins, that is to say protein A, G or L which has been modified compared with the wild-type, for example formed by artificial or natural gene mutations.

Aptamers according to the invention which are specific for protein A, G or L, substances comprising protein A, G or L or microorganism comprising protein A, G or L can be obtained, for example, by the SELEX process (Systematic Evolution of Ligands by Exponential Enrichment). Fundamental works on the SELEX process originate from Tuerk and Gold, Science 249 (1990) 505-510, and Ellington and Szostak, Nature 346 (1990) 818-822. SELEX processes are furthermore disclosed in U.S. Pat. No. 5,567,588 and U.S. Pat. No. 5,270,163.

In the SELEX process, a combinatory random library comprising single-stranded DNA (ssDNA) oligonucleotides is first produced. The oligonucleotides have an internal variable region having, for example, 40-60 nucleotides, which is flanked by primer regions on the 5' and 3' end. The primer regions serve as primer binding sites for a PCR amplification. Combinatory random libraries can be obtained from commercial suppliers. The variability of a library lies for example in the region of approx. $10^{15}$ different molecules. Starting from the single-stranded DNA oligonucleotide library, the oligonucleotides which bind best to the target are enriched via various selection and amplification steps in cycles. Each cycle comprises the following part steps:

a) binding of the oligonucleotides to the target,
b) washing of the oligonucleotide-target complexes to remove non-bound oligonucleotides,
c) elution of the oligonucleotides bound to the target,
d) amplification of the eluted oligonucleotides by means of PCR,
e) purification of the relevant ssDNA oligonucleotides from the PCR product.

After each cycle the selected and enriched oligonucleotide pool is used as the starting material for the next cycle. 8 to 12 cycles are advantageously performed.

A SELEX process for isolation of aptamers according to the invention is described in more detail in the attached examples. An example of a process for discovering aptamers according to the invention is the so-called FluMag-SELEX process in which fluorescence-labeled ssDNA molecules and small magnetic spheres (beads) are employed as an immobilizing matrix for the target. This process, which was used in the attached examples, is also described in: R. Stoltenburg et al. (2005) FluMag-SELEX as an advantageous method for DNA aptamer selection, Anal. Bioanal. Chem. 383, 83-91.

After analysis of the sequence, aptamers according to the invention and variants, mutants, fragments and derivatives thereof, which are described further in the following, can be prepared using conventional techniques of chemical DNA and RNA synthesis which are known to the person skilled in the art. If the sequence of a DNA aptamer is known, an RNA aptamer having the same sequence can be prepared by conventional synthesis methods. Furthermore, the binding properties of individual aptamers to the target can be investigated.

Preferably, the aptamers according to the invention are synthetic oligonucleotides which have been selected in particular by the SELEX process just described from an underlying synthetic, combinatory oligonucleotide library or are subsequently prepared using conventional synthesis methods.

In a specific embodiment the invention relates to an aptamer which binds to protein A, G or L, substances comprising protein A, G or L or microorganisms comprising protein A, G or L and which is chosen from the group consisting of a) an aptamer comprising or consisting of a nucleic acid sequence which is chosen from the group consisting of SEQ ID NO: 1 to SEQ ID NO: 65, with the proviso that thymine can be replaced by uracil,
b) an aptamer, the nucleic acid sequence of which has an identity of at least 70% with the nucleic acid sequence of an aptamer from a),
c) an aptamer which hybridizes with the complementary strand of an aptamer from a), d) an aptamer in which, compared with an aptamer from a), one or more nucleotides are substituted, deleted, inserted and/or added, e) a fragment of an aptamer according to a), b), c) or d), and f) a derivative of an aptamer according to a), b), c), d) or e).

The functionality of the aptamers from a)-f), that is to say the binding to protein A, G or L, substances comprising protein A, G or L or microorganisms comprising protein A, G or L can be estimated using a secondary structural analysis of the aptamers. The functionality of other variants mentioned in this description can also be estimated in this way. The possible secondary structure of the aptamers can be modeled utilizing the program "mfold" (version 3.1 or 3.5) available for free on the internet. This program performs an analysis of the two-dimensional structure with the aid of an energy-minimizing method (Zuker M., 2003, Nucleic Acid Research 31, 3406-3415). When the aptamers are folded, stars (double-stranded regions), loops, e.g. outward loops of single-stranded regions, such as hairpin or internal loops, and bulbs, i.e. small single-stranded bulges in double-stranded regions, may occur. Using the mfold program the hypothetical secondary structure for an aptamer nucleotide sequence is determined under standard conditions (binding/folding temperature: 21° C., ionic strength of the binding buffer: [$Na^+$] 100 nM/[$Mg^{2+}$] 10 nM). Binding buffer composition: 100 mM NaCl, 20 mM Tris-HCl, pH 7.6, 10 mM $MgCl_2$, 5 mM KCl, 1 mM $CaCl_2$. The person skilled in the art can very easily draft a large number of variants of the aptamers according to the invention described concretely with sequences, for example by substitution, insertion or deletion of individual bases. Such variants can be analyzed for their secondary structure by computer, as described above, in large numbers and without experimental outlay. If agreement exists between the secondary structure of a variant and the secondary structure of an aptamer described concretely with a sequence, a functionality of the variant is probable or sometimes very probable.

Variants of the aptamers according to claim 1a) are explained in the following.

The invention includes aptamers of which the sequence has an identity of at least 70%, preferably at least 80%, or at least 85%, or at least 90%, or at least 93%, or at least 95%, or at least 96%, or at least 97%, and most preferably at least 98% with one of the sequences of SEQ ID NO: 1 to SEQ ID NO: 65.

In connection with the present invention, the term "identity" is to be understood as meaning the number of coinciding nucleotides (identity), expressed in percent. Preferably, the identity between two nucleic acid sequences in question is determined with the aid of computer programs. If sequences which are compared with one another have different lengths, the identity is to be determined such that the number of nucleotides which has the shorter sequence together with the longer sequence determines the percentage content of the identity. Preferably, the identity is determined by means of the known computer program ClustalW2, which is available to the public. In this invention reference is expressly made to the definition of identity in the ClustalW2 program and the method for its determination, which are accessible to the public.

ClustalW2 is available to the public from the European Bioinformatics Institute (EBI) of the European Molecular Biology Laboratory (EMBL) and can be downloaded from the internet at http://www.ebi.ac.uk/Tools/msa/clustalw2/. When the ClustalW2 computer program is used to determine the identity between e.g. the nucleotide sequence of the nucleic acid molecules described in the context of the present invention and the nucleotide sequence of other nucleic acid molecules, the following parameters are set: DNA Weight Matrix: IUB; GAP OPEN: 10; GAP EXTENSION: 0.20; GAP DISTANCES: 5; NO END GAPS: no; ITERATION: none; NUMITER: 1; CLUSTERING: NJ.

The invention also provides any aptamer which hybridizes with the complementary strand of an aptamer according to the invention described above, provided that such an aptamer binds to protein A, G or L, a substance comprising protein A, G or L or an organism comprising protein A, G or L, in particular *Staphylococcus aureus, Streptococcus* or *Peptostreptococcus*.

In the context of this invention the term "hybridization" means a hybridization under conventional hybridization conditions, preferably under stringent conditions, such as are described, for example, in Sambrook et al., Molecular Cloning, A Laboratory Manual, 3rd ed. (2001) Cold Spring Harbor Laboratory Press, Cold Spring Harbor, N.Y.

Nucleic acid molecules which can hybridize with the molecules mentioned can be isolated, for example, from DNA libraries. The identification and isolation of such nucleic acid molecules in this context can be carried out using the nucleic acid molecules mentioned (SEQ ID NO: 1 to SEQ ID NO: 65) or parts of these molecules or of the reverse complements of these molecules, e.g. by means of hybridization by standard methods (see e.g. Sambrook et al., 2001, Molecular Cloning, A Laboratory Manual, 3rd ed. Cold Spring Harbor Laboratory Press, Cold Spring Harbor, N.Y.). Fragments used as a hybridization probe can also be synthetic fragments or oligonucleotides which have been prepared with the aid of the usual synthesis techniques and the sequence of which essentially coincides with that of an aptamer described in the context of the present invention or of a complementary strand thereof.

The invention also provides an aptamer which is derived from an aptamer having one of the sequences of SEQ ID NO: 1 to SEQ ID NO: 65 such that in one of the sequences of SEQ ID NO: 1 to SEQ ID NO: 65 one or more nucleotides are substituted, removed (deleted), added within the sequence (inserted) and/or added at the 5' end and/or 3' end, wherein such an aptamer binds to protein A, G or L, a substance comprising protein A, G or L or an organism comprising protein A, G or L, in particular *Staphylococcus aureus, Streptococcus* or *Peptostreptococcus*. Aptamers modified in this way preferably have an identity of at least 70%, or at least 80%, or at least 85%, or at least 90%, or at least 93%, or at least 95%, or at least 96%, or at least 97%, and most preferably at least 98% with one of the sequences of SEQ ID NO: 1 to SEQ ID NO: 65. The term identity has been defined above. A sequence in which one or more nucleotides are substituted is also called a substitution mutant, a sequence in which one or more nucleotides are deleted is called a deletion mutant and a sequence in which one or more nucleotides are inserted is called an insertion mutant. Preferably, overall, based on substitution, deletion and insertion in an aptamer molecule, up to 60 nucleotides are substituted, deleted and/or inserted, more preferably up to 50 nucleotides, still more preferably up to 40 nucleotides, or up to 30 nucleotides, particularly preferably up to 10 nucleotides or up to 8 nucleotides or up to 5 nucleotides, furthermore preferably up to 3 nucleotides and most preferably up to 2 nucleotides.

In the case of an addition, preferably up to 100 nucleotides are added at the 5' and/or at the 3' end of the aptamer, more preferably up to 50 nucleotides, still more preferably up to 40 nucleotides, or up to 20 nucleotides, particularly preferably up to 10 nucleotides or up to 8 nucleotides, most preferably up to 5 nucleotides.

In a specific embodiment, in the modifications described under points b) to f) one or both of the motifs ATACCAGCT-TATTCAATT (SEQ ID NO: 66) and ACAATCGTAAT-CAGTTAG (SEQ ID NO: 67) remain unchanged or essentially unchanged. Essentially unchanged means that up to a maximum of 5 nucleotides, preferably a maximum of 4 nucleotides, most preferably a maximum of 3 nucleotides in this motif are substituted, deleted and/or inserted.

In the case of an aptamer in which, compared with an aptamer which comprises a nucleic acid sequence which is chosen from one of SEQ ID NO: 1 to SEQ ID NO: 65, one or more nucleotides are added, additions can be made on the 5' end of the aptamer and/or on the 3' end of the aptamer. Additions can be, for example, oligonucleotides which serve as spacers between the aptamer sequence and a labeling or an oligonucleotide which has a sequence which is complementary to a labeled oligonucleotide, as described in WO2005113817. Various further sequences which can be added which do not impair the binding properties of the aptamer to its target are known to the person skilled in the art in the field of SELEX processes, for example from Conrad et al., "In Vitro Selection of Nucleic Acid Aptamers That Bind Proteins", Methods in Enzymology, 267: 336-83 (1996); Ciesiolka et al., "Affinity Selection-Amplification from Randomized Ribooligonucleotide Pools", Methods in Enzymology, 267: 315-35 (1996); and Fitzwater et al., "A SELEX Primer", Methods in Enzymology, 267: 275-301 (1996).

Fragments, also called parts or part sequences, have the functionality of the aptamers according to the invention which is described above. Fragments are obtained by removing one or more nucleic acids at the 5' end and/or at the 3' end of an aptamer according to the invention. Fragments preferably have a length of at least 10, in particular of at least 15 and particularly preferably of at least 20 nucleotides, most preferably at least 30 or at least 40 nucleotides. Fragments are, for example, those aptamers in which the motif ATACCAGCT-TATTCAATT (SEQ ID NO: 66) and/or ACAATCGTAAT-CAGTTAG (SEQ ID NO: 67) are completely or partially removed.

In connection with the present invention, the term "derivative" means an aptamer which has a chemical structure which does not occur in natural DNA or RNA.

In particular, the term derivative means an aptamer which comprises a chemical structure which deviates from deoxyribose, ribose, phosphate, adenine (A), guanine (G), cytosine (C), thymine (T) or uracil (U). An aptamer derivative can be modified on the nucleobase, on the pentose or on the phosphate backbone.

In particular, the term "derivative" describes an aptamer
in which nucleotides occurring naturally in DNA and RNA are replaced partially or completely by nucleotides which deviate chemically therefrom, so-called modified nucleotides, and/or
the molecule structure of which is modified in another manner, in particular by binding to structures which do not occur naturally in RNA or DNA, and/or
which have a modified backbone.

Specific examples of derivatives are, without being limited thereto,
Aptamers which have on at least one nucleotide an alkylation, arylation or acetylation, alkoxylation, halogenation, an amino group or another functional group. Examples of modified nucleotides are 2'-fluororibonucleotides, 2'-NH$_2$—, 2'-OCH$_3$— and 2'-O-methoxy-ethyl-ribonucleotides, which are used for RNA aptamers, Aptamers which have a base modification, such as bromouridine, Labeled aptamers, also called marked aptamers. Preferred labelings (labels) are detectable visually, optically, photonically, electronically, acoustically, opto-acoustically, according to weight, electrochemically, electrooptically, spectrometrically, enzymatically or otherwise chemically, biochemically or physically. Labels can be, for example, bound reporter, marker or adapter molecules. Examples of these are labeled aptamers, the labeling of which can be detected by luminescence, UV/VIS coloring, enzymatically, electrochemically, immunologically or radioactively. Examples of labeling substances are given below in the explanation of methods according to the invention in which labeled aptamers can be employed.

Aptamers which comprise enantiomeric nucleotides.

Aptamers which are present completely or partially as phosphorothioate RNA or DNA, phosphorodithioate RNA or DNA, phosphoroselenoate RNA or DNA, phosphorodiselenoate RNA or DNA, phosphoroamidate RNA or DNA, locked nucleic acid (LNA), peptide nucleic acid (PNA), N3'-P5' phosphoroamidate RNA/DNA, cyclohexene-nucleic acid (CeNA), tricyclo-DNA (tcDNA) or spiegelmer, or which comprise phosphoroamidate-morpholine (PMO) components (see also Chan et al., Clinical and Experimental Pharmacology and Physiology (2006) 33, 533-540).

By some of the modifications, aptamers can be stabilized against nucleic acid-cleaving enzymes. In the stabilizing of the aptamers, a distinction can be made in principle between the subsequent modification of the aptamers and the selection with already modified RNA/DNA. The stabilizing does not affect the affinity of the modified RNA/DNA aptamers, but prevents rapid decomposition of the aptamers in an organism or biological solutions by RNases/DNases. In the context of the invention an aptamer is described as stabilized if the half-life in biological sera is greater than one minute, preferably greater than one hour, particularly preferably greater than one day. The aptamers can also be modified with reporter molecules which, in addition to detection of the labeled aptamers, can also contribute towards increasing the stability.

In a further specific embodiment the invention relates to an aptamer which binds to protein A, G or L, substances comprising protein A, G or L or microorganisms comprising protein A, G or L and which is chosen from the group consisting of
a) an aptamer comprising or consisting of a nucleic acid sequence having the SEQ ID NO: 62, with the proviso that thymine can be replaced by uracil,
b) an aptamer, the nucleic acid sequence of which has an identity of at least 70% with the nucleic acid sequence of an aptamer from a), in particular an aptamer having a sequence according to SEQ ID NO: 1 to SEQ ID NO: 4,
c) an aptamer which hybridizes with the complementary strand of an aptamer from a), in particular an aptamer having a sequence according to SEQ ID NO: 1 to SEQ ID NO: 4,
d) an aptamer in which, compared with an aptamer from a), one or more nucleotides are substituted, deleted, inserted and/or added, in particular an aptamer having a sequence according to SEQ ID NO: 1 to SEQ ID NO: 4,
e) a fragment of an aptamer according to a), b), c) or d), and
f) a derivative of an aptamer according to a), b), c), d) or e).

Regarding points b)-f), the above disclosures also apply analogously to the embodiments which are still to follow.

In a further specific embodiment the invention relates to an aptamer which binds to protein A, G or L, substances comprising protein A, G or L or microorganisms comprising protein A, G or L and which is chosen from the group consisting of
  a) an aptamer comprising or consisting of a nucleic acid sequence having the SEQ ID NO: 63, with the proviso that thymine can be replaced by uracil,
  b) an aptamer, the nucleic acid sequence of which has an identity of at least 70% with the nucleic acid sequence of an aptamer from a), in particular an aptamer having a sequence according to SEQ ID NO: 5 to SEQ ID NO: 8,
  c) an aptamer which hybridizes with the complementary strand of an aptamer from a), in particular an aptamer having a sequence according to SEQ ID NO: 5 to SEQ ID NO: 8,
  d) an aptamer in which, compared with an aptamer from a), one or more nucleotides are substituted, deleted, inserted and/or added, in particular an aptamer having a sequence according to SEQ ID NO: 5 to SEQ ID NO: 8,
  e) a fragment of an aptamer according to a), b), c) or d), and
  f) a derivative of an aptamer according to a), b), c), d) or e).

In still a further specific embodiment the invention relates to an aptamer which binds to protein A, G or L, substances comprising protein A, G or L or microorganisms comprising protein A, G or L and which is chosen from the group consisting of
  a) an aptamer comprising or consisting of a nucleic acid sequence having the SEQ ID NO: 64, with the proviso that thymine can be replaced by uracil,
  b) an aptamer, the nucleic acid sequence of which has an identity of at least 70% with the nucleic acid sequence of an aptamer from a), in particular an aptamer having a sequence according to SEQ ID NO: 9 to SEQ ID NO: 10,
  c) an aptamer which hybridizes with the complementary strand of an aptamer from a), in particular an aptamer having a sequence according to SEQ ID NO: 9 to SEQ ID NO: 10,
  d) an aptamer in which, compared with an aptamer from a), one or more nucleotides are substituted, deleted, inserted and/or added, in particular an aptamer having a sequence according to SEQ ID NO: 9 to SEQ ID NO: 10,
  e) a fragment of an aptamer according to a), b), c) or d), and
  f) a derivative of an aptamer according to a), b), c), d) or e).

In still a further specific embodiment the invention relates to an aptamer which binds to protein A, G or L, substances comprising protein A, G or L or microorganisms comprising protein A, G or L and which is chosen from the group consisting of
  a) an aptamer comprising or consisting of a nucleic acid sequence having the SEQ ID NO: 65, with the proviso that thymine can be replaced by uracil,
  b) an aptamer, the nucleic acid sequence of which has an identity of at least 70% with the nucleic acid sequence of an aptamer from a), in particular an aptamer having a sequence according to SEQ ID NO: 11 to SEQ ID NO: 12,
  c) an aptamer which hybridizes with the complementary strand of an aptamer from a), in particular an aptamer having a sequence according to SEQ ID NO: 11 to SEQ ID NO: 12,
  d) an aptamer in which, compared with an aptamer from a), one or more nucleotides are substituted, deleted, inserted and/or added, in particular an aptamer having a sequence according to SEQ ID NO: 11 to SEQ ID NO: 12,
  e) a fragment of an aptamer according to a), b), c) or d), and
  f) a derivative of an aptamer according to a), b), c), d) or e).

A specific embodiment of the invention relates to an aptamer which binds to protein A, G or L, substances comprising protein A, G or L or microorganisms comprising protein A, G or L and which is chosen from the group consisting of
  a) an aptamer comprising or consisting of a nucleic acid sequence which is chosen from the group consisting of SEQ ID NO: 1 to SEQ ID NO: 65, wherein
    at the 5' end of the nucleic acid sequence of SEQ ID NO: 1 to SEQ ID NO: 65 an oligonucleotide having the sequence 5' ATACCAGCTTATTCAATT 3' (SEQ ID NO: 66) is removed and/or
    at the 3' end of the nucleic acid sequence of SEQ ID NO: 1 to SEQ ID NO: 65 an oligonucleotide having the sequence 5' ACAATCGTAATCAGTTAG 3' (SEQ ID NO: 67) is removed,
    with the proviso that thymine can be replaced by uracil,
  b) an aptamer, the nucleic acid sequence of which has an identity of at least 70% with the nucleic acid sequence of an aptamer from a),
  c) an aptamer which hybridizes with the complementary strand of an aptamer from a),
  d) an aptamer in which, compared with an aptamer from a), one or more nucleotides are substituted, deleted, inserted and/or added,
  e) a fragment of an aptamer according to a), b), c) or d), and
  f) a derivative of an aptamer according to a), b), c), d) or e).

Examples of sequences for this are given in the examples as SEQ ID NO: 69-71. In particular, the invention includes embodiments in which at the 3' end of the nucleic acid sequence of SEQ ID NO: 1 to SEQ ID NO: 65 an oligonucleotide having the sequence 5' ACAATCGTAATCAGTTAG 3' (SEQ ID NO: 67) is removed.

The binding capacity of the aptamers according to the invention is described by the affinity (sensitivity) of the binding (expressed by the dissociation constant).

In a further aspect, the invention relates to a medicament, in particular for the diagnosis, prophylaxis and/or treatment of diseases which are to be attributed to *Staphylococcus aureus, Streptococcus* and/or *Peptostreptococcus*, comprising one or more different aptamers according to the invention as described above. The term prophylaxis can mean, for example, that *Staphylococcus aureus, Streptococcus* or *Peptostreptococcus* are rendered harmless by binding to an aptamer according to the invention and an infection of an organism is thereby prevented.

The invention furthermore also relates to the use of the aptamers according to the invention for the diagnosis, prophylaxis, treatment and/or therapy of diseases which are to be attributed to *Staphylococcus aureus, Streptococcus* or *Peptostreptococcus*, and the use of the aptamers according to the invention for the preparation of a medicament for the diagnosis, prophylaxis, treatment and/or therapy of diseases which are to be attributed to *Staphylococcus aureus, Streptococcus* or *Peptostreptococcus*.

A medicament in the context of the invention is any agent which can be employed in the prophylaxis, diagnosis, therapy, control of progress or after-treatment of patients who show at least occasionally a pathogenic modification of overall state or of the state of individual parts of the patient's organism. The medicament can be an medicament for humans and also for animals. Diseases which are to be attributed to *Staphylococcus aureus* and can be treated with a medicament according to the invention are, in particular, sepsis, skin and wound infections, pneumonias, abscesses, furuncles, carbuncles, endocarditis, muscular diseases (pyomyositis), osteomyelitis, food poisonings by *S. aureus* exotoxins, toxic shock syndrome (TSS), and sepsis and mastitis in animals.

The medicament according to the invention preferably comprises pharmaceutically acceptable auxiliary substances and/or carrier substances which are known to the person skilled in the art.

The medicament can comprise the aptamer, for example, as a pharmaceutically acceptable salt. These can be, for example, salts of inorganic acids, such as e.g. of phosphoric acid, or salts or organic acids. The particular dose or the dose range for administration of the medicament according to the invention is high enough for the desired prophylactic or therapeutic effect of the binding to protein A, G or L to be achieved. In general, the dose will vary with the age, the constitution and the sex of the patient, and will take into account the severity of the disease. It goes without saying that the specific dose, frequency and duration of the administration moreover depend on a large number of factors, such as e.g. the binding capacity of the aptamers, dietary habits of the individual to be treated, nature of administration, rate of excretion and combination with other medicaments. The exact dose can be determined by a person skilled in the art using known means and methods.

To assist in the medicinal action, in a preferred embodiment of the invention the medicament can also comprise further active compounds, such as e.g. antibodies.

The medicament of the present invention can be used orally, transmucosally, rectally, pulmonally, enterally and/or parenterally. A direct injection into the body is preferred. The type of administration chosen depends on the indication, the dose to be administered, individual-specific parameters etc. In particular, the various types of administration render possible a site-specific therapy which minimizes side effects and reduces the dose of active compound. Preferred injections are the intradermal, subcutaneous, intramuscular or intravenous injection. The administration can be effected e.g. with the aid of so-called vaccination guns, which introduce the DNA into the skin by means of gold beads, or by means of syringes, which introduce the DNA under the skin or into the muscle. It is also possible to provide the aptamer as an aerosol which is inhaled by the organism, preferably a human patient.

In order to increase the protective or therapeutic action of the aptamers according to the invention, pharmaceutically acceptable auxiliary substances, such as e.g. adjuvants, can be added to the pharmaceutical compositions prepared therefrom. In the context of the invention any substance which, with the DNA aptamers according to the invention, renders possible, intensifies or modifies an action is an adjuvant. Known adjuvants are, for example, aluminum compounds, such as e.g. aluminum hydroxide or aluminum phosphate, saponins, such as e.g. QS 21, muramyl dipeptide or muramyl tripeptide, proteins, such as e.g. gamma-interferon or TNF, MF 59, phosphatidylcholine, squalene or polyols. DNA which has an immunostimulatory property or which codes a protein having an adjuvant effect, such as e.g. a cytokine, can furthermore be administered in parallel or in a construct.

The pharmaceutical composition can be present, for example, as a tablet, capsule, powder, solution, dispersion or suspension. The presentation forms of the pharmaceutical composition are prepared in a suitable dosage and in a manner known per se using the conventional solid or liquid carrier substances and/or diluents and the auxiliary substances conventionally employed, according to the desired type of administration.

In a further aspect the invention relates to a method for the detection of protein A, G or L, substances comprising protein A, G or L or microorganisms comprising protein A, G or L, in particular *Staphylococcus aureus, Streptococcus* or *Peptostreptococcus*, in which a) one or more different aptamers according to the invention, as described above, is brought into contact with a sample which comprises protein A, G or L, the substance or microorganism comprising protein A, G or L or the microorganism and b) binding between the aptamer(s) and protein A, G or L, or between the aptamer(s) and the substance, or between the aptamer(s) and the microorganism is detected.

The method can be either a qualitative or a quantitative detection method. Method steps a) and b) can be carried out simultaneously or essentially simultaneously, depending on the concrete design of the method.

The method is suitable in particular for use in the analysis of foodstuffs, water and the environment, water treatment and water processing, in particular for drinking water and waste water, diagnostics and for use in hospitals and care institutions.

The method is suitable in particular for detection of *Staphylococcus aureus* in any desired media and environments, in particular in water and other liquids, such as, for example, in drinking and waste water samples. In the case of *Staphylococcus aureus*, the aptamer according to the invention binds to protein A, which occurs in the cell wall and is accessible to the aptamer. The aptamer can likewise bind to other germs which comprise protein A, G or L, for example as a surface protein in the cell wall. If protein A, G or L do not sit on the surface of the microorganism, there is the possibility of destroying the organism in order to release the protein A, G or L contained therein for detection.

A sample in the context of the above detection method is a material which is provided or is obtained by taking samples and which is assumed to comprise protein A, G or L, a substance comprising protein A, G or L or a microorganism comprising protein A, G or L (summarized as "target" or in the context of this detection method also as "analyte"), and which is to be tested for the presence of the target.

A sample can be a water sample, in particular a drinking water, ground water, surface water or waste water sample, a sample of material taken elsewhere from the environment, a clinical sample or a foodstuff sample.

A sample can furthermore be all biological materials which have been isolated from individuals, for example biological tissue and fluids, which include inter alia blood, skin, plasma, serum, lymph, urine, cerebral fluid, tears, smears, tissue samples, organs and tumors. In the present case, samples also include constituents of cell cultures. The sample is taken, in particular, such that the part amount removed corresponds to an average of the total amount. The features determined by analysis of the sample serve to evaluate the amount recorded by the sample, which in turn allows conclusions to be drawn regarding the total amount, for example the blood or the lymph in an organism. For the analysis, the samples can be pretreated, such as e.g. by mixing, addition of enzymes or labels, or purified.

When the aptamer is brought into contact with the target (protein A, G or L, substance comprising protein A, G or L or microorganism comprising protein A, G or L), an aptamer-target complex forms by binding of the aptamer to the target. The binding or the binding event can be detected, for example, visually, optically, photonically, electronically, acoustically, opto-acoustically, according to weight, electrochemically, electrooptically, spectrometrically, enzymatically or otherwise chemically, biochemically or physically.

In the case of a labeling-free detection, the aptamer is fixed, for example, on to a surface and the change in the layer thickness after adding on of the target is determined using one of the methods mentioned, such as e.g. via a change in the optical properties of the sensor layer (e.g. refractive index). A further method for labeling-free detection is measurement of the change in weight after binding of the aptamer to the target using a microbalance, or measurement of a change in frequency of vibrating quartz after binding of the aptamer to the target, which is provided on the surface of the vibrating quartz.

In cases where the complexing is not directly detectable, the complex can be rendered visible by labeling, for example in an indicator reaction after direct or indirect coupling of a complexing partner with a labeling substance. Either the aptamer used or the target can be provided with a labeling (label). Preferably, the aptamer is labeled.

Preferred labelings (labels) can be detected visually, optically, photonically, electronically, acoustically, opto-acoustically, according to weight, electrochemically, electrooptically, spectrometrically, enzymatically or otherwise physically, chemically or biochemically. In one embodiment of the method the labeling is detected by luminescence, UV/VIS spectroscopy, enzymatically, electrochemically or radioactively.

Luminescence relates to the emission of light. In the method according to the invention, for example, photoluminescence, chemiluminescence and bioluminescence are used to detect the labeling. In the case of photoluminescence or fluorescence, excitation takes place by absorption of photons. Examples of fluorophores are, without limitation, bisbenzimidazole, fluorescein, Acridine Orange, Cy5, Cy3 or propidium iodide, which can be covalently coupled to aptamers, tetramethyl-6-carboxyrhodamine (TAMRA), Texas Red TR, rhodamine, Alexa Fluor dyestuffs (inter alia fluorescent dyestuffs of various wavelengths from various companies). The evaluation is effected visually or using appropriate measuring apparatus, e.g. in a Multilabel Counter, in a fluorescence microscope, or by flow cytometry, e.g. in a cytofluorimeter. Chemiluminescence describes the emission of visible light as a consequence of a chemical reaction. Bioluminescence describes the emission of visible light as a consequence of an enzyme reaction, for example a redox reaction catalyzed by the enzyme luciferase.

Other labeling substances are catalysts, colloidal metallic particles, e.g. gold nanoparticles, colloidal non-metallic particles, quantum dots, organic polymers, latex particles, or liposomes with signal-generating substance. Colloidal particles can be detected colorimetrically.

Visually detectable dyestuffs, such as, for example, intercalating dyestuffs, can also be employed.

Enzymes of which the enzymatic reaction is characterized by the consumption or the formation of detectable substrates or products can also be employed as labels, wherein, without limitation, an optical or electrochemical detection can be used. A detection can be conducted e.g. with enzymes as labeling substances which convert substrates into colored products, preferably peroxidase, green fluorescent protein (GFP), luciferase, [beta]-galactosidase or alkaline phosphatase. For example, the colorless substrate X-Gal is converted by the activity of [beta]-galactosidase into a blue product, the coloring of which is recorded visually.

An abovementioned enzymatic label and detection system uses alkaline phosphatase. Various detections are possible with alkaline phosphatase (AP), as described by way of example in the following:

electrochemical detection: substrate phenyl phosphate, enzymatic reaction of APP forms phenol, is detected electrochemically on a phenol sensor (e.g. using immobilized tyrosinase)

measurement of the color reaction: substrate p-nitrophenyl phosphate, enzymatic reaction of APP forms p-nitrophenol, is colored yellow fluorescence detection: substrate 4-methylumbelliferonyl phosphate, enzymatic reaction of APP forms the methylumbelliferonyl radical, which releases fluorescence after excitation for chemiluminescence detection: substrate AMPPD (3-(2'-spiroadamantane)-4-methoxy-4-(3"-phosphoryloxy)phenyl-1,2-dioxetane), enzymatic reaction of APP forms AMP D and releases hv (chemiluminescence)

APP furthermore converts 5-bromo-4-chloro-3-indolyl phosphate (BCIP or X-phosphate) and nitro blue tetrazolium salt (NBT) in a colored reaction. In this context the dyestuffs precipitate out in the immediate vicinity of the AP molecules and stain the surroundings of the bound compounds dark violet.

Peroxidase catalyzes e.g. the oxidation of ABTS (2,2'-azino-bis-[3-ethylbenzothiazoline-6-sulfonic acid]) in the presence of $H_2O_2$. Because of the enzyme stability and a large number of possible substrates, horseradish peroxidase is preferred. Further enzyme labels which catalyze the generation of detectable products are chloramphenicol acetyltransferase (CAT) and glutathione S-transferase (GST).

The detection can also be carried out by means of radioactive isotopes with which the aptamer is labeled, preferably 3H, 14C, 32P, 33P, 35S or 125I, particularly preferably 32P, 33P or 125I. In scintillation counting, the radioactive radiation emitted by the radioactively labeled aptamer-target complex is measured indirectly. A scintillator substance is excited by the radioactive radiation. During the transition into the base state, the excitation energy is released again as flashes of light, which are amplified by a photoelectron multiplier (photomultiplier) and counted.

The aptamers can also be labeled with digoxigenin or biotin, which, for example, are bound by antibodies or streptavidin, which in turn can carry a labeling, such as e.g. an enzyme conjugate. If the antibody is coupled to an enzyme, an ELISA (enzyme-linked immunosorbent assay) can be carried out for the detection, which is explained further in the following. The prior covalent linking (conjugation) of an antibody with an enzyme can be carried out in various known ways. The detection of the antibody binding can also be carried out radioactively in an RIA (radioactive immunoassay) using radioactive isotopes, preferably with 125I, or by fluorescence in an FIA (fluoroimmunoassay) using fluorophores, preferably using fluorescein or FITC.

The methods mentioned preferably include washing steps, in order to separate off non-bound and/or non-specifically bound aptamers and/or detection reagents. The procedure for all the detection methods is known to the person skilled in the art. Direct detection of the labeling is preferred in the present method of the invention, in particular direct detection by fluorescence.

In a further embodiment of the method, the detection is carried out in situ. This reaction requires a suitable incubation chamber on which the detection can be easily carried out and rendered visible. A solid carrier which renders it possible to fix the sample, aptamers and where appropriate detection reagents of the complexes is advantageously used for this. The aptamers can be applied to the solid carrier either before or after the sample. Methods of immobilizing the abovementioned aptamers are known to the person skilled in the art.

Examples are given below. All the detections which have already been mentioned above, such as labeling-free detections and detections using a labeling, are possible for the detection. In the case of a color detection, the aptamers can be labeled such that reading off and evaluation can be realized directly after the incubation.

In the methods explained above and all other methods disclosed by this invention, the aptamers according to the invention can be employed by themselves, or a mixture of various aptamers according to the invention can be employed. Aptamers according to the invention can also be used in combination with other aptamers. A combination with other aptamers for other targets (i.e. targets other than protein A, G or L, substances comprising protein A, G or L and microorganism comprising protein A, G or L) offers the advantage that an appropriate method can be used simultaneously also for the detection, enrichment, separating off and/or isolation of other targets.

As already mentioned, the sample or the aptamer can be immobilized on a solid phase, depending on the design of the method. For example, (micro)arrays of the aptamer according to the invention or microtiter plate test systems can be employed in the method.

Aptamers bind to the target with a similar strength to that of antibodies to their target (antigen). The detection method described above can therefore be carried out analogously to known immunoassays, wherein compared with a known immunoassay one or more antibodies can be replaced by an aptamer according to the invention.

For example, it is possible to carry out the detection method in the form of a competitive assay or a sandwich assay.

In one embodiment of a competitive assay an aptamer according to the invention which is specific for the target is bound to a solid phase. The sample solution, which comprises the target to be measured and to which at the same time a known concentration of labeled target is added, is then added. Both the non-labeled target present in unknown concentration in the sample solution and the labeled target compete for binding to the bound aptamer. The higher the concentration of the target in the sample, the less labeled target is accordingly bound to the aptamer. The detection of the target in the sample and the measurement of its concentration are possible via the recognition and where appropriate a quantitative determination of the labeling.

In another embodiment of a competitive assay, an aptamer according to the invention which is specific for the target is likewise first bound to a solid phase. Labeled target is bound thereto. Measurement of the labeling gives the starting signal. The addition of sample with non-labeled target displaces bound labeled target, and the decreasing measurement signal is proportional to the sample concentration.

In a conventional immunological sandwich assay, at least two antibodies are employed. One of the two antibodies is first immobilized on a solid phase. This is called the primary antibody or also captor. After addition of the sample the antigen contained therein binds to the primary antibody. The sample solution is then removed and the second antibody, called secondary antibody or detector, is introduced on to the solid phase in dissolved form. The detector now likewise binds to the antigen bound by the primary antibody. For detection and quantification, either the antibody is labeled itself, or it is detected via a labeled reagent. In the present invention, this method is modified in that either the primary antibody or the secondary antibody or both are replaced by an aptamer according to the invention, and in that the antigen is a target for the aptamer, that is to say protein A, G or L, a substance comprising protein A, G or L or a microorganism comprising protein A, G or L. The assay can be carried out with all the known solid phases, for example microtiter plates, strips, membranes, cells etc.

In a specific embodiment, the invention thus provides a method for the detection of protein A, G or L, substances comprising protein A, G or L or microorganisms comprising protein A, G or L, in particular *Staphylococcus aureus, Streptococcus* or *Peptostreptococcus*, in which a) a first antibody or an aptamer according to the invention which is specific for protein A, G or L is immobilized on a solid phase, b) the solid phase with the antibody or aptamer immobilized thereon is incubated with a sample which comprises protein A, G or L, the substance comprising protein A, G or L or the microorganism comprising protein A, G or L and c) the solid phase is incubated with a second antibody or an aptamer according to the invention which is specific for protein A, G or L and d) binding between the second antibody or the aptamer and protein A, G or L, substances comprising protein A, G or L or microorganism comprising protein A, G or L is detected under the condition that at least one of steps a) or c) an aptamer according to the invention is employed instead of an antibody.

The immobilizing in step a) can be carried out using all the conventional techniques which are also known from immunological assays. In the case of an antibody, the detection in step d) can be carried out by the known methods which are known from immunological direct and indirect sandwich assays. Either the antibody itself can be labeled, for example by binding to an enzyme which can catalyze a color reaction for the detection, or a third antibody can be added, which in its turn binds to the second antibody and has a labeling. If an aptamer is employed in step c), this is preferably a labeled aptamer which can be detected using suitable detection reactions, as already described above. Washing steps are preferably carried out between the steps a)-d) mentioned, e.g. using conventional and known wash buffers. In this method the term immobilizing means that the antibody immobilized in step a) or the aptamer is not removed from the solid phase by a washing step.

In a further aspect the invention relates to a method for the enrichment, separating off and/or isolation of protein A, G or L, substances comprising protein A, G or L or microorganisms comprising protein A, G or L, in particular *Staphylococcus aureus, Streptococcus* or *Peptostreptococcus*, in which a) one or more different aptamers, as described above, is/are brought into contact with a sample which comprises protein A, G or L, a substance comprising protein A, G or L or a microorganism comprising protein A, G or L, wherein a complex or complexes of the aptamer(s) and protein A, G or L, of the aptamer(s) and the substance comprising protein A, G or L or of the aptamer(s) and the microorganism comprising protein A, G or L is formed, b) the complex(es) and the remainder of the sample are separated from one another, and c) optionally protein A, G or L, the substance comprising protein A, G or L or the microorganism comprising protein A, G or L is isolated from the complex.

A "sample" in the context of this method is defined in the same way as a sample in the sense of the detection method described above. A sample is, in particular, a water sample, such as, for example, a drinking water, ground water, surface water or waste water sample, a sample of material taken elsewhere from the environment, or a foodstuff sample.

This method is also employed in particular for use in the analysis of foodstuffs, water and the environment, water treatment and the environment, in particular for drinking water and waste water, diagnostics, and in hospitals and care institutions.

A "separating off" of protein A, G or L, substance comprising protein A, G or L or of a microorganism comprising protein A, G or L (summarized as "target") from a sample can be, in the context of the analytical detection limit, complete or incomplete. A complete separating off is also called "removal" herein. Using this method, in particular *Staphylococcus aureus, Streptococcus* or *Peptostreptococcus* can be separated off from surroundings where it is undesirable, for example from aqueous or other liquid samples.

An "enrichment" is achieved in step b) when the aptamer-target complex formed and the remainder of the sample are separated from one another. Two fractions are obtained, wherein the complex is enriched in the fraction which comprises the complex. The term "enrichment" can relate to the complex which is formed from the aptamer and protein A, G or L, from the aptamer and the substance comprising protein A, G or L or from the aptamer and the microorganism comprising protein A, G or L, or to the protein A, G or L itself, the substance itself comprising protein A, G or L or the microorganism itself comprising protein A, G or L (summarized as "target"), i.e. the target without the aptamer. For enrichment of the target, method step c) can be carried out. In other words, an enrichment means an increase in the concentration of the aptamer-target complex or of the target itself.

The term "isolation" can relate to the complex which is formed from the aptamer and protein A, G or L, from the aptamer and the substance comprising protein A, G or L or from the aptamer and the microorganism comprising protein A, G or L, or to the protein A, G or L itself, the substance itself comprising protein A, G or L or the microorganism itself comprising protein A, G or L. The last method step is therefore optional.

The separating off, enrichment and isolation described above can be realized simultaneously using the method. Preferably, however, the method is carried out for one of these purposes.

The term "complex" means the structure which is formed on binding of the aptamer to its target. The term "complex" thus means an aptamer-target structure in which the aptamer is bound to the target. As explained in the introduction, the aptamer-target binding predominantly, but not necessarily exclusively, takes place via the structure compatibility, so-called "stacking interactions" in aromatic ring structures (stacking forces by electron interaction with adjacent bases), electrostatic interactions (e.g. van der Waals, ionic, dipole forces) and hydrogen bridge bonds.

Depending on the design of the method, the method steps a), b) and c) mentioned can be carried out simultaneously, and in particular method steps a) and b) can be carried out simultaneously.

In the bringing of the target and aptamer into contact, the formation of the aptamer-target complex can be promoted by temperature control at the optimum aptamer-target binding temperature, preferably 20-25° C., and/or stirring of the sample. After an incubation time, the aptamer-target complexes are separated off from the remainder of the sample solution. Suitable methods are known to the person skilled in the art, such as e.g. dialysis, ultrafiltration, gel filtration, chromatography, magnetic separation or washing steps, if the complex is present in immobilized form.

By changes in the defined conditions required for the aptamer binding, the aptamer-target complex is separated in optional step c). Physicochemical influences, such as e.g. a variation in the salt concentration or pH or a heat-related denaturing, are conceivable for this. Finally a further purification of the target is possible, wherein the aptamer can be degraded beforehand, e.g. by acid (thermal) hydrolysis or DNases. If the aptamer is immobilized, the target can be eluted, such as e.g. from a column, which is then regenerated and reused.

According to the invention, the aptamers can also be immobilized on a solid phase, more precisely on the surface of a solid phase, preferably via a spacer molecule, which can be, for example, a linker nucleic acid. Suitable methods of immobilization are known to the person skilled in the art and can be accompanied both by a covalent coupling and by a non-covalent coupling by means of suitable affinity pairs, such as e.g. biotin/streptavidin. The solid phase can be, for example, plates, strips, membranes, films, gels, beads and micro- and nanoparticles. Examples of carrier materials are inorganic and organic polymers, ceramics, glasses, metals, in particular noble metals. These include plastics, for example based on polystyrene. Biopolymers, preferably cellulose, dextran, agar, agarose and Sephadex, which can be functionalized, in particular as nitrocellulose or cyanobromide-Sephadex, can furthermore be employed as polymers in the method according to the invention. Aptamers can be bound to magnetic beads, the surfaces of which are functionalized e.g. with tosyl or epoxy groups, with amino or carboxyl groups or with streptavidin. Coupling of magnetic beads to the deoxyribose of the aptamers, such as e.g. via a hydrazone bond, is furthermore possible. The examples of polymers are non-limiting and others are also conceivable. Preferred combinations of geometric form and material are gels of biopolymers, in particular agarose, and gel matrices of dextran and Sephadex, which—for example packed in columns—form hollow cavities of defined pore size. In a specific embodiment the separating off, enrichment and/or isolation method just described is an affinity chromatography method in which an aptamer according to the invention is immobilized on a solid phase, preferably on small spheres (beads) or another type of chromatography column material, wherein all geometric forms of a solid phase can be used and all the abovementioned substances can be employed by way of example.

Using aptamer-modified surfaces, the corresponding targets can be enriched starting from low concentrations.

The invention also relates to the use of the aptamer described above for the detection, enrichment, separating off and/or isolation of protein A, G or L, substances comprising protein A, G or L or microorganisms comprising protein A, G or L, in particular *Staphylococcus aureus, Streptococcus* or *Peptostreptococcus*. In particular, the aptamer can be employed in the methods explained above. The term enrichment also includes the purification of the target.

In a further aspect the invention also relates to methods for the quantification of the binding of an immunoglobulin to protein A, G or L, wherein in the method
  a) protein A, G or L or a microorganism comprising protein A, G or L is provided,
  b) the immunoglobulin is added to protein A, G or L or the microorganism comprising protein A, G or L,
  c) the mixture produced in b) is brought into contact with an aptamer according to the invention,
  d) the amount of aptamer bound is determined and the amount of immunoglobulin bound is determined therefrom.

Various process variants are conceivable:

In one variant the immunoglobulin mentioned binds to the same epitope of protein A, G or L as the aptamer according to the invention. The term "epitopes" then means that these are the same epitopes which occur in several instances because several protein A, G or L molecules are employed in the method and/or because protein A, G or L has several epitopes of the same type. In step c) of the method the aptamer binds to protein A, G or L molecules to which no immunoglobulin has bound. The amount of protein A, G or L bound is determined in step d), for example via the intensity of a fluorescence labeling. The binding site can be determined in an array of protein A, G or L by the recognizable labeling site.

In another variant the aptamer and the immunoglobulin bind to different epitopes. Nevertheless, due to steric hindrance the aptamer no longer binds in step c) to protein A, G or L molecules to which immunoglobulin has already bound. In step c) of the method the aptamer binds to protein A, G or L molecules to which no immunoglobulin has bound.

In connection with the above method, the invention also relates to the use of the aptamer described above for the quantification of the binding of immunoglobulins to protein A, G or L. This use and the associated method are suitable in particular as an assay for medical diagnostics.

The provision of protein A, G or L or the microorganism comprising protein A, G or L can be effected in various ways. For example, protein A, G or L or the microorganism comprising protein A, G or L can be provided in a liquid phase in a defined amount. It is also possible to immobilize the aptamer in a defined amount on a solid phase or to immobilize protein A, G or L or the microorganisms in a defined amount on a solid phase. The solid phase can be, for example, plates, such as, for example, microtiter plates, strips, membranes, films, gels, beads and micro- and nanoparticles.

In step b) an immunoglobulin which binds to protein A, G or L or to protein A, G or L present in the cell wall of the microorganism is then added. The antibody is conventionally suspended in a liquid phase.

If protein A, G or L or the microorganism is bound to a solid phase, after step b) non-bound antibody is preferably removed by washing, for example with a suitable wash buffer.

After step b), and optionally a washing step, protein A, G or L molecules/microorganisms coated with antibody and protein A, G or L molecules/microorganisms which are not coated with antibody are obtained, called "mixture" here. In the next step the mixture is brought into contact with aptamer according to the invention. The aptamer binds to protein A, G or L molecules/microorganisms which are not coated with antibody.

After step c) non-bound aptamer is preferably removed by washing, for example with a suitable wash buffer.

In the last step it is determined how much aptamer has bound to protein A, G or L or the microorganism. Binding between the aptamer and protein A, G or L or the microorganism can be detected as already explained above in the detection method according to the invention. Preferably, a labeled aptamer is employed.

A further use of the aptamer according to the invention relates to the use for blocking or quantifying free binding sites on protein A, G or L. There are commercially available surfaces modified with protein A, G or L, such as small spheres (beads) or microtiter plates.

If the surface modified with protein A, G or L is used for the immobilization of substances which bind protein A, G or L, the aptamers can be used for blocking the protein A-, G- or L-binding sites which remain free after the immobilization. A prerequisite of this is that the aptamer and the other substance which binds protein A, G or L have the same binding site in protein A, G or L or are mutually influenced in their binding capacity.

In certain uses it may also be desirable to coat protein A, G or L with aptamer on the surface, so that no other substances, in particular immunoglobulins, can bind thereto.

Likewise, the aptamers can be used for quantification of the binding sites which have remained free after the immobilization, or in other words for checking the surface coating.

In a further aspect the invention also relates to an aptamer probe for the detection of protein A, G or L, substances comprising protein A, G or L or microorganisms comprising protein A, G or L, in particular *Staphylococcus aureus, Streptococcus* or *Peptostreptococcus*, wherein the probe comprises an aptamer according to the invention and a labeling agent (label). The labeling agent can be bound to the aptamer in various ways, for example, and non-limitatively, by covalent bonding, complexing, DNA/RNA hybridization. For example, a labeling agent can be bound to an aptamer according to the invention as described in WO2005113817. WO2005113817 describes an aptamer having an added oligonucleotide tail and a linker oligonucleotide, which carries a label, wherein the sequence of the linker oligonucleotide is complementary to the sequence of the oligonucleotide tail of the aptamer, so that the linker oligonucleotide hybridizes on the oligonucleotide tail of the aptamer and the aptamer is labeled with the label. A further possibility is the binding of biotin to the aptamer and the binding of labeling agent to streptavidin. The labeling agent is bound to the aptamer by biotin-streptavidin binding.

All labeling agents which can be bound to DNA or RNA can be employed in principle. Concrete examples of labeling substances have been given above in the explanation of methods according to the invention in which labeled aptamers can be employed. For example, the labeling is a dyestuff. In a specific variant, the labeling agent is a substance which renders possible generation of an image by the labeled aptamer in an imaging method. The image can be generated by radiation which generates an image directly visible to the human eye, or by radiation which is not directly visible, for example x-rays or radioactive radiation which is rendered visible in another manner, for example on a film. Labeling agents can be, for example, luminescent, phosphorescent, fluorescent, radioactive or UV/VIS labeling substances. The probe according to the invention can be employed in particular for the detection, enrichment, separating off and/or isolation methods explained in this description, in particular in assays for detection of protein A, G or L or microorganisms comprising protein A, G or L, such as *Staphylococcus aureus, Streptococcus* or *Peptostreptococcus*. Assays can be e.g. direct and indirect sandwich assays.

In a further aspect the invention relates to a biosensor which comprises an aptamer according to the invention.

According to the present invention, such a biosensor preferably comprises the following elements:
- a receptor comprising or consisting of an aptamer according to the invention, and
- a transducer which converts the binding event between the aptamer and target into an electrically quantifiable signal.

Further elements, such as, for example, a signal processing device, an electronic output system, a display device, a data processing device, a data memory and interfaces to other equipment, can moreover be present.

The biological receptor of the aptamer biosensor preferably comprises the aptamer according to the invention in immobilized form or consists of only the aptamer in immobilized form. The function of the receptor is recognition of the analyte based on a biochemical mechanism, here the binding of the aptamer according to the invention to its target (protein A, G or L, substance comprising protein A, G or L, microorganism comprising protein A, G or L). From a sample which is brought into contact with the biosensor, for example a complex mixture which comprises the target, the target can be identified and quantified via the specific binding of the aptamer.

The specificity of the biosensor is determined by the receptor, while the sensitivity of the sensor is predominantly influenced by the transducer used. The aptamer-target binding which takes place on the receptor is converted by the transducer into an electronically evaluable signal. The transducer converts the signal from the selective recognition reaction of the biosensor (binding of target on aptamer), which is proportional to the concentration of the target in the sample, into an electrically quantifiable measurement signal. The signal formation takes place on the basis of the molecular interaction between the target and the aptamer.

Using a biosensor according to the invention, qualitative, quantitative and/or semiquantitative analytical information can preferably be obtained. It is suitable in particular for use in the analysis of foodstuffs, water and the environment, water treatment and water processing, in particular for drinking water and waste water, in diagnostics and for use in hospitals and care institutions.

The coupling between the receptor and transducer takes place preferably by the immobilization of the aptamer on the transducer surface, for example via streptavidin-biotin binding, wherein the aptamer is preferably bonded to biotin and the surface of the transducer comprises immobilized streptavidin.

The binding of the target to the aptamer according to the invention can be measured, for example, via optical, microgravimetric, thermal or acoustic transducers, preferably via optical or microgravimetric transducers.

The measurement in optical transducers can be based on principles of photometry, wherein, for example, changes in color or luminescence intensity are recorded. The optical methods include measurement of fluorescence, phosphorescence, bioluminescence and chemoluminescence, infrared transitions and light scattering. The optical methods also include measurement of changes in layer thickness when the target is bound to the aptamer. The change in layer thickness can be measured e.g. by means of surface plasmon resonance (SPR) or reflectometric interference spectroscopy (RIfS). The interference on thin layers (reflectometric interference spectroscopy) and the change in the evanescent field can furthermore be measured.

Microgravimetric transducers are, for example, QCM sensors (quartz crystal microbalance) which detect a change in weight when the target is bound to the aptamer.

Acoustic transducers utilize the changes in frequency of piezoelectric vibrating quartz, which highly sensitively detects the changes in weight which occur when the target binds to the aptamer. The quartz crystal used is placed in an oscillating electrical field and the resonance frequency of the crystal is measured. A change in weight on the surface of the vibrating quartz, e.g. by reaction of the analyte with the receptor previously immobilized on the crystal surface, has the effect of a change in the resonance frequency, which can be quantified.

Electrochemical transducers can measure e.g. the change in concentration of redox-active labels on the electrode surface, or the change in concentration of redox-active substrates or products which e.g. are consumed or formed in the enzymatic reaction of an enzyme label.

Thermal transducers measure the heat effect of the aptamer-target binding reaction.

In a further aspect the invention relates to a solid phase, also called a solid carrier, in particular for use in the detection, enrichment, separating off and/or isolation of protein A, G or L, substances comprising protein A, G or L or microorganisms comprising protein A, G or L, on which an aptamer according to the invention is immobilized.

An example of a biosensor is explained in the attached embodiment example. The person skilled in the art can find instructions for the construction of further biosensors in Cho, E. J., Lee, J.-W., Ellington, A. D. (2009): Applications of Aptamers as Sensors, Annual Review of Analytical Chemistry 2: 241-264; Mok, W and Li, Y. (2008): Recent Progress in Nucleic Acid Aptamer-Based Biosensors and Bioassays, Sensors 8: 7050-7084; Song, S., Wang, L., Li, J., Fan, C., Zhao, J. (2008): Aptamer-based biosensors, TrAC Trends in Analytical Chemistry 27: 108-117.

Solid phases are conceivable in all possible geometric forms. Examples of solid carriers are plates, strips, membranes, microtiter plates, films, gels, microparticles, nanoparticles or beads. Particularly suitable materials from which a solid phase can be produced are inorganic polymers, organic polymers, glasses, organic and inorganic crystals, ceramics, metals, in particular noble metals, and semiconductors. A particularly suitable organic polymer is a polymer based on polystyrene. Biopolymers, preferably cellulose, dextran, agar, agarose and Sephadex, which can be functionalized, in particular as nitrocellulose or cyanobromide-Sephadex, can furthermore be employed as polymers. Aptamers can be bound to small magnetic spheres (magnetic beads) which carry e.g. carboxy-terminated or epoxy-activated side chains. Coupling of magnetic beads to the ribose or deoxyribose of the aptamers, such as e.g. via a hydrazone bond, is furthermore possible. The examples of polymers are non-limiting and other molecules are conceivable. Preferred combinations of geometric form and material are gels of biopolymers, in particular agarose, and gel matrices of dextran and Sephadex, which—for example packed in columns—form hollow cavities of defined pore size. In a specific embodiment the solid carrier with the immobilized aptamer is a stationary phase for affinity chromatography, wherein the carrier preferably has the form of spheres or particles of other shape.

In a specific embodiment the solid phase is a test strip which comprises one or more different aptamers according to the invention. The test strip can be employed in particular for qualitative, semiquantitative and quantitative assays which operate with visual detection methods, in particular for lateral flow assays.

A lateral flow assay operates as follows: A liquid sample which presumably comprises a target for the aptamer according to the invention is applied to one site on the strip or the strip is wetted with the sample at one site. This site is the so-called sample application zone of the strip. The strip comprises a matrix material, through which the liquid test medium and the target suspended or dissolved therein can flow by capillary action from a sample application zone into a detection zone, where a detectable signal or the absence of such a signal indicates the presence of the target.

The strip which can be employed for lateral flow assays comprises one or more aptamers according to the invention, for example in the sample application zone or at least still in a position before the detection zone. If the target is present in the test sample, it forms a complex with the aptamer present in the strip, which flows to the detection zone and is detected there. In other words, the target flows within the strip to the aptamer and forms a complex with this, which then flows to the detection zone.

The binding reaction can also take place directly on the application site if e.g. the test strip comprises the aptamer and the aptamer-target binding is rendered visible directly using an appropriate label.

Preferably, a labeled aptamer is employed, wherein any labeling already described above can be employed. Preferably, a labeling which leads to a visually detectable signal in the detection zone of the test strip is employed. In principle, the presence or the absence of the target in the sample can be determined by detection or lack of detection of a labeled aptamer in the detection zone.

In one embodiment of a test strip, an enzyme-labeled aptamer is employed. The target present in the sample forms with the enzyme-labeled aptamer a complex which flows along the strip to a detection zone which comprises a substrate for the enzyme label, which is capable of generating a colored reaction in the presence of the enzyme label. The strip preferably comprises a further zone in which the target is immobilized, so that labeled aptamer which, because of the absence of sufficient target in the sample, is not combined with the target is held and is thereby prevented from reaching the detection zone.

In a further embodiment the test strip functions according to the principle of an immunological lateral flow assay, for example a pregnancy test strip, wherein a labeled immunoglobulin used there is replaced by a preferably labeled aptamer according to the invention.

A specific variant functions according to the following principle: A test strip is wetted with sample and target present in the sample binds to a dyestuff-labeled aptamer. The target-aptamer-dyestuff complex migrates to the detection zone, in which is fixed a second antibody which likewise binds to the target. The immobilized antibody binds the migrating target-aptamer-dyestuff complex in the detection zone and this is stained. Excess dyestuff-labeled aptamer migrates further to a control zone in which is fixed a substance which binds the dyestuff-labeled aptamer and is thereby stained.

The test strip can be produced from any material which can be wetted with a sample and into which an aptamer according to the invention can be introduced. Materials though which a sample and a target contained therein can flow by capillary action are preferred in particular. Examples are nitrocellulose, nitrocellulose mixtures with polyester or cellulose, non-sized paper, porous paper, viscose filament, glass fibers, acrylonitrile copolymer or nylon, and all further materials which are conventional in lateral flow assays.

The test strip can already be used as such in order to establish the presence of target in a sample. For use, the strip can be immersed in a sample, and in the case of a lateral flow assay, for example, with only one end, which then serves as the sample application zone.

The invention also provides a lateral flow assay device which comprises the test strip described above. In addition to the test strip, the device can comprise, for example, a housing into which the test strip is embedded and which comprises a preferably closable opening to the sample application zone of the test strip, and openings for observation of a detection and if appropriate a control zone. Such a construction is known from the field of pregnancy tests and known structures of a lateral flow assay device can correspondingly also be used in the present invention.

In another specific embodiment, the solid carrier and the aptamer form a microarray or a so-called "DNA or RNA chip", which can have one channel or several channels. In the microarray, one or more aptamers and reference materials for base signal compensation or function testing can be arranged at several measurement points arranged to form an array. In a multichannel chip this arrangement is effected in the individual channels. Parallel multiple measurement of a sample or, in the case of various aptamers, parallel measurement of different analytes in a sample is thereby possible.

The immobilization of the aptamer on the solid phase can be carried out in various ways and in any manner known to the person skilled in the art for immobilizing DNA or RNA on solids. Known possibilities have already been mentioned above in this description. The immobilization of aptamers on nanoparticles is described e.g. in WO2005/13817. A solid phase of paper or a porous material can be wetted with the aptamer in the liquid phase and the liquid phase can then be evaporated, so that the aptamer remains in the paper or the porous material.

In a further aspect the present invention also relates to kit comprising an aptamer according to the invention.

The kit preferably comprises an aptamer according to the invention, in particular a labeled aptamer according to the invention or an aptamer probe according to the invention, and further components for the reaction intended with the kit or the method to be carried out with the kit, for example components for an intended detection, enrichment, separating off and/or isolation method. Examples are buffer solutions, substrates for a color reaction, dyestuffs or enzymatic substrates. The aptamer and/or further components can be immobilized on a solid phase. Examples of forms and materials for solid phases have already been mentioned elsewhere in this description. The solid phase can be provided, for example, in the form of a (micro)array or a microtiter plate. In the concrete case, the solid phase can be an immobilized captor substance for protein A, G or L, substance comprising protein A, G or L or a microorganism comprising protein A, G or L, in particular an immobilized antibody, which serves to bind protein A, G or L, a substance comprising protein A, G or L or a microorganism comprising protein A, G or L. The immobilized captor substance is preferably arranged in the form of a (micro)array, in a microtiter plate or in chips.

The kit serves preferably for carrying out a detection, enrichment, separating off and/or isolation method according to the invention for protein A, G or L, substance comprising protein A, G or L or a microorganism comprising protein A, G or L, or for carrying out other types of assay with the aid of an aptamer according to the invention. In this respect, reference is made to the preceding disclosure.

The aptamer can be provided in the kit in the most diverse forms, for example freeze-dried or in a liquid medium.

The invention also relates to a measuring apparatus for the detection of protein A, G or L, substances comprising protein A, G or L or microorganisms comprising protein A, G or L. The measuring apparatus comprises one or more different aptamers described above, an aptamer probe as described above or a biosensor as described above. The measuring apparatus can moreover comprise, inter alia, a sampling device, a signal processing device, a display device for reading off measurement results or measurement values, a data processing device, a data storage device and interfaces for connection with external equipment or storage media.

Using the measuring apparatus, depending on the design, qualitative, quantitative and/or semiquantitative analytic information on the target to be measured can be obtained. The detection methods explained above can be carried out using the measuring apparatus. It is suitable in particular for use in the analysis of foodstuffs, water and the environment, water treatment and water processing, in particular for drinking water and waste water, in diagnostics and for use in hospitals and care institutions.

The measuring apparatus is, in particular, a transportable measuring apparatus which can be employed on site, for example a lightweight measuring apparatus in pocket format.

The sampling device of the measuring apparatus can be constructed in various ways. In one variant the sampling device is a capillary or a porous strip in which liquids can be sucked up. For sampling, such a sampling device is conventionally immersed in a liquid sample. The sample is transported by capillary force to the desired location in the measuring apparatus, at which the aptamer is to be found and where the detection reaction can take place. For example, the sample is transported to a biosensor which comprises the aptamer and which in its turn generates a measurement signal.

In another variant, the sampling device comprises a hose or a tube and a pump. With the pump, a liquid sample is sucked in and the sample is transported to the desired location in the measuring apparatus, at which the aptamer is to be found and where the detection reaction can take place. For example, the sample is transported to a biosensor which comprises the aptamer and which in its turn generates a measurement signal.

In one aspect the invention also relates to the use of a probe described above, a solid phase described above, a biosensor described above, a test strip described above, a lateral flow assay device described above, a kit described above, or a measuring apparatus described above for the detection of protein A, G or L, substances comprising protein A, G or L or microorganisms comprising protein A, G or L, or for enrichment, separating off and/or isolation of protein A, G or L, substances comprising protein A, G or L or microorganisms comprising protein A, G or L. Reference is made here to all the method variants described above.

The invention is explained in more detail in the following with the aid of non-limiting examples of concrete embodiments. Standard reagents and buffers which are free from contamination are used in the example experiments.

EXAMPLE 1

Preparation of the Target-Modified Magnetic Beads

Dynabeads® M-280 Streptavidin (Invitrogen, UK) were used in accordance with the manufacturer's instructions. $1 \times 10^9$ magnetic beads were first washed 3× with 500 µl of PBS, pH 7.4 each time and then incubated with 510 µg of biotinylated protein A for 1 h at 21° C., while shaking (native, biotinylated protein A from *Staphylococcus aureus* (Sigma, P2165); dissolved in 0.1 M sodium phosphate buffer pH 7.4 to give a stock solution of 2 mg/ml). Further washing steps then followed: 3×500 µl of PBS, pH 7.4; 1×500 µl of PBS, pH 7.4+0.05% Tween20 with an incubation of 5 min at 21° C., while shaking; 1×500 µl of PBS, pH 7.4+0.05% Tween20 (without incubation); 2×500 µl of PBS, pH 7.4. The beads were separated off from the solutions each time using a Magnetic Separation Stand (Promega, Germany). The protein A-modified beads were then suspended in 500 µl of PBS, pH 7.4+0.02% sodium azide and the suspension was stored at 4° C.

EXAMPLE 2

In Vitro Selection (FluMag-SELEX)

The selection of DNA aptamers for protein A was carried out using the FluMag-SELEX process. For this, biotinylated protein A was immobilized on streptavidin-functionalized magnetic beads and employed in this form as the target for the aptamer selection. A fluorescein labeling of the DNA from the second SELEX round onwards moreover rendered possible quantification thereof in the various steps of the SELEX process by means of fluorescence measurement (Wallac Victor²V Multilabel Counter; PerkinElmer, Germany; measurement conditions: excitation 485 nm/emission 535 nm, time 1 s, CW lamp energy 22500, measurement volume 100 µl/well, measurement in black 96-well microtiter plates (NUNC; Germany)).

The starting point of the selection process was a randomized DNA oligonucleotide library which was produced by means of chemical synthesis (Microsynth AG, CH): 5'-ATACCAGCTTATTCAATT-$N_{40}$-ACAATCGTAAT-CAGTTAG-3'. $N_{40}$ represents the region having variable nucleotides (random sequence).

All the oligonucleotides of this library have specific sequences on the 5' and 3' end which serve as primer binding sites for amplification of the oligonucleotides by means of PCR. The following modified PCR primers were used:
as sense primer 5'-Fl-ATACCAGCTTATTCAATT-3' (see SEQ ID NO: 66) having a fluorescein (Fl) labeling on the 5' end and as antisense primer 5'-d$A_{20}$HEGL-CTAACTGAT-TACGATTGT-3' having a lengthening on the 5' end (d$A_{20}$=20 nucleotides with the base adenine; HEGL=hexaethylene glycol spacer, for the primer sequence see SEQ ID NO: 68).

For the aptamer selection, successive SELEX rounds comprising several steps were carried out: the selection steps—(i) binding of the DNA oligonucleotide library (~2.5 nmol of ssDNA) or of the oligonucleotide pool selected in the preceding round to the target-modified magnetic beads (incubation for 30 min at 21° C., while shaking, in binding buffer [100 mM NaCl, 20 mM Tris-HCl, pH 7.6, 10 mM $MgCl_2$, 5 mM KCl, 1 mM $CaCl_2$]; binding volume 250 µl), (ii) separating off of the non-bound oligonucleotides by several washing steps on the binding complexes, (iii) elution of the bound oligonucleotides by means of heat (2× incubation of the binding complexes in 250 µl of binding buffer for 10 min at 95° C., while shaking); the amplification step—(iv) multiplication of the eluted oligonucleotides by means of PCR and the purification step—(v) separation of the double-stranded PCR products and obtaining of the relevant DNA single strands (sense strands) by means of denaturing PAGE and subsequent gel elution. The new oligonucleotide pool generated in this manner at the end of a SELEX round was employed for a renewed binding reaction with the target-modified magnetic beads in the next SELEX round. In each SELEX round a fresh aliquot of ~$10^8$ target-modified magnetic beads was used here. A negative selection step was additionally inserted in rounds 3 and 7-11. This means that the oligonucleotides were first incubated with streptavidin-functionalized magnetic beads (without target) in order to remove all oligonucleotides which bind non-specifically to the immobilization matrix. The oligonucleotides remaining in the supernatant were then subjected to binding with the target-modified magnetic beads (see selection step—(i)). After a stepwise enrichment of target-binding oligonucleotides, in particular in rounds 8-11 (see FIG. 1), the SELEX process was ended in the 11th round after the amplification step, in this case using non-modified primers.

The attached FIG. 1 shows the course of the SELEX process for selection of aptamers which bind protein A. The amount of oligonucleotides binding to the target-modified magnetic beads in each SELEX round is shown. A negative selection step was additionally carried out in rounds 3 and 7-11 (identified in FIG. 1 with the * symbol). The amount of oligonucleotides which bind to the immobilization matrix of the target is likewise shown (0-0.07 pmol), but was often at the detection limit of the fluorescence measurement.

EXAMPLE 3

Cloning and Sequencing

In the last 11th SELEX round the oligonucleotides selected (aptamer pool) were amplified with non-modified primers in order subsequently to clone the PCR products formed directly into the vector pCR2.1-TOPO and to transform them into *E. coli* TOP10 cells (TOPO TA Cloning Kit; Invitrogen, UK). Positive clones were identified by means of colony PCR. Using the QIAprep 96 Turbo Miniprep Kit (Qiagen, Germany), the plasmid DNA of some of the clones was prepared and sent for sequencing of the aptamer insert (Microsynth AG, CH).

An overview of the aptamer sequences obtained from the cloning is given in Table 1. The primer sequence (sense) at the 5' end is ATACCAGCTTATTCAATT (SEQ ID NO: 66) and the primer binding region for the antisense primer at the 3' end is ACAATCGTAATCAGTTAG (SEQ ID NO: 67). They are in each case shown in bold. The sequences with SEQ ID NOs: 66 and 67 are a constituent of the aptamers, subject to shortened sequences, as defined in the preceding general description. The "Number" column indicates the number of clones having an identical aptamer sequence. When several clones having an identical sequence were found, the aptamer designation is marked in bold (see e.g. PA#2/8).

Some aptamers can be classified into groups on the basis of their sequences. Within a group, nucleotides which deviate compared with the representative of a group are identified by underlining. The sequences combined into a group are identical apart from point mutations and deletions or are to be derived from the representative. The aptamer number of the representative of a group is identified by underlining (see e.g. aptamer no. PA#2/8 for group 1).

The aptamers can be classified into groups on the basis of their sequences. Nucleotides which deviate within a group are identified by underlining.

The sequence with SEQ ID NO: 62 combines the sequences of group 1 and shows variable nucleotides underlined.

The sequence with SEQ ID NO: 63 combines the sequences of group 2 and shows variable nucleotides underlined.

The sequence with SEQ ID NO: 64 combines the sequences of group 3 and shows variable nucleotides underlined.

The sequence with SEQ ID NO: 65 combines the sequences of group 4 and shows variable nucleotides underlined.

In SEQ ID NO: 65 $X_1$ denotes either A or L, wherein L represents no nucleotide (deletion).

Table 2 shows an overview of the nucleotide symbols which represent one or more of the nucleotides A, G, C or T.

TABLE 1

| Aptamer no. | Aptamer sequence (5'-3') | SEQ ID NO. | Number |
|---|---|---|---|
| Group 1 | | | |
| PA#2/8 | ATACCAGCTTATTCAATTAGCAACATGAGGGGGATAGAGGGGGTGGGTTCTCTCTGCTACAATCGTAATCAGTTAG | 1 | 4 |
| PA#2/16 | ATACCAGCTTATTCAATTAGCAACATGAGGGGGATAGAGGGGGTGGGTTCTCTCG<u>R</u>CTACAATCGTAATCAGTTAG | 2 | 1 |
| PA#6/48 | ATACCAGCTTATTCAATTAGCAACATGAGGGGGATA<u>A</u>AGGGGGTGGGTTCTCTCG<u>G</u>CTACAATCGTAATCAGTTAG | 3 | 1 |
| PA#6/58 | ATACCAGCTTATTCAATTAGCAACATGAGGGGGAT<u>G</u>GAGGGGGTGGGTTCTCT<u>T</u>GGCTACAATCGTAATCAGTTAG | 4 | 1 |
| | ATACCAGCTTATTCAATTAGCAACATGAGGGGGAT<u>RR</u>AGGGGGTGGGTTCTCT<u>YGR</u>CTACAATCGTAATCAGTTAG | 62 | |
| Group 2 | | | |
| PA#4/34 | ATACCAGCTTATTCAATTCCCCAACGAGTCGATATGTAGCCCACACTCTGATTCGTCCACAATCGTAATCAGTTAG | 5 | 3 |
| PA#2/9 | ATACCAGCTTATTCAATT<u>GC</u>ACAACGAGTCGATATGTAGCCCACACTCTGATTCGTCCACAATCGTAATCAGTTAG | 6 | 1 |
| PA#10/71 | ATACCAGCTTATTCAATTCCCCAACGAGTCGATATGTAGCCCACA<u>TT</u>CTGATTCGTCCACAATCGTAATCAGTTAG | 7 | 1 |
| PA#10/76 | ATACCAGCTTATTCAATT<u>A</u>CCCAACGAGTCGATATGTAGCCCACACTCTGATTCGTCCACAATCGTAATCAGTTAG | 8 | 1 |
| | ATACCAGCTTATTCAATT<u>VCM</u>CAACGAGTCGATATGTAGCCCACA<u>Y</u>TCTGATTCGTCCACAATCGTAATCAGTTAG | 63 | |
| Group 3 | | | |
| PA#2/6 | ATACCAGCTTATTCAATTACCGATCACTAGCCGACTAATTGGTTTCCGATCGCAGTCCACAATCGTAATCAGTTAG | 9 | 2 |
| PA#6/54 | ATACCAGCTTATTCAATTACCGATCACTA<u>C</u>CCGACTAATTGGTTTCCGATCGCAGT<u>TC</u>ACAATCGTAATCAGTTAG | 10 | 1 |
| | ATACCAGCTTATTCAATTACCGATCACTAGCCGACTAATTGGTTTCCGATCGCAGT<u>Y</u>CACAATCGTAATCAGTTAG | 64 | |
| Group 4 | | | |
| PA#14/82 | ATACCAGCTTATTCAATTCCACAACCGAACTCGTAAGACGTATGTAGCCGCCAACTGTACAATCGTAATCAGTTAG | 11 | 2 |
| PA#2/18 | ATACCAGCTTATTCAATTCC-CAACCGAACTCGTAAGACGTATGTAGCCGCCAACTGTACAATCGTAATCAGTTAG | 12 | 1 |
| | ATACCAGCTTATTCAATTCC<u>X<sub>1</sub></u>CAACCGAACTCGTAAGACGTATGTAGCCGCCAACTGTACAATCGTAATCAGTTAG | 65 | |
| Further aptamers | | | |
| PA#4/22 | ATACCAGCTTATTCAATTGCAGTACTGATGAGTGTAGCCGTATGATTATCGTTTGTGGACAATCGTAATCAGTTAG | 13 | 8 |
| PA#2/11 | ATACCAGCTTATTCAATTGGAGACGACAAACTATTACGTACTACGGCATGCACTTGGTACAATCGTAATCAGTTAG | 14 | 6 |
| PA#2/3 | ATACCAGCTTATTCAATTCGACAAGTGGGCATTACGATTCTAGCCCTGATTATGTTCCACAATCGTAATCAGTTAG | 15 | 3 |
| PA#6/52 | ATACCAGCTTATTCAATTACGCATTGGAGCCCGAAACTGATTCATTGAGCCTACCTGTACAATCGTAATCAGTTAG | 16 | 2 |
| PA#2/14 | ATACCAGCTTATTCAATTACGACCGTAGACGACTTACACTGATGTTGCGCATTTCTGTACAATCGTAATCAGTTAG | 17 | 2 |
| PA#4/31 | ATACCAGCTTATTCAATTCGATGACGACTGTAGCCGCAATACGCCCTGTTACGTTGTACAATCGTAATCAGTTAG | 18 | 2 |
| PA#6/41 | ATACCAGCTTATTCAATTGGACGCCGACTAACTTTACGTGGTTCTCCTACCGCCTAACCACAATCGTAATCAGTTAG | 19 | 2 |
| PA#6/43 | ATACCAGCTTATTCAATTACGAAATGTAGCCGATCCTGATTACTCTCTGTCAGCTTGGACAATCGTAATCAGTTAG | 20 | 2 |

TABLE 1-continued

| Aptamer no. | Aptamer sequence (5'-3') | SEQ ID NO. | Number |
|---|---|---|---|
| PA#2/4 | ATACCAGCTTATTCAATTGGAGTCCGACTAAATGATCTTTGAGAGTGTCTCACAGTCACAATCGTAATCAGTTAG | 21 | 1 |
| PA#2/5 | ATACCAGCTTATTCAATTGCAGATTACGCCTTGTAGCCCGCACTGATCTCGATATTTGGACAATCGTAATCAGTTAG | 22 | 1 |
| PA#2/7 | ATACCAGCTTATTCAATTACGAGGTACGATTACAGACGATCGAACTGATACTTGTTGGACAATCGTAATCAGTTAG | 23 | 1 |
| PA#2/10 | ATACCAGCTTATTCAATTACGATCACTGTAGACGGCGACTGATTAATCTACGTATTGGACAATCGTAATCAGTTAG | 24 | 1 |
| PA#2/12 | ATACCAGCTTATTCAATTGCAATGGACCCCAAAGTTGGATTGTAGCCGCTGCTGTTCGACAATCGTAATCAGTTAG | 25 | 1 |
| PA#2/13 | ATACCAGCTTATTCAATTACGGCAACGAGTGTAGACCGACGCTGATTACTGTCTCATCGACAATCGTAATCAGTTAG | 26 | 1 |
| PA#2/17 | ATACCAGCTTATTCAATTGCACCAACCCGCTGATAGGATGTAGCCGCTAACTCCTTCCACAATCGTAATCAGTTAG | 27 | 1 |
| PA#4/25 | ATACCAGCTTATTCAATTGGAGACGACGCCTGGTTTCGTTATTGAGTGTCTCTGCCACAATCGTAATCAGTTAG | 28 | 1 |
| PA#4/29 | ATACCAGCTTATTCAATTGGAGCCGCAAATATCGTGATGAATGTGTGAGCCGATCTACACAATCGTAATCAGTTAG | 29 | 1 |
| PA#4/30 | ATACCAGCTTATTCAATTACCCCGATGTAGCCGACGTGCACTTGTTATGATTAGGACCACAATCGTAATCAGTTAG | 30 | 1 |
| PA#4/28 | ATACCAGCTTATTCAATTCCAGAACCGGCGATTGTAACCGACTAAGTGTGCATGATCCACAATCGTAATCAGTTAG | 31 | 1 |
| PA#4/39 | ATACCAGCTTATTCAATTGCAGCCGACTAACCTGATGAGTGTGGTCAGTTTACGCTTGACAATCGTAATCAGTTAG | 32 | 1 |
| PA#4/40 | ATACCAGCTTATTCAATTGGAGACGACGCGGCTGATTATGTTAGTCTGTAACCCCACCACAATCGTAATCAGTTAG | 33 | 1 |
| PA#6/46 | ATACCAGCTTATTCAATTACGAACATGGAGCCGCACTGATTACTGGTCCACCGCGTACACAATCGTAATCAGTTAG | 34 | 1 |
| PA#6/47 | ATACCAGCTTATTCAATTGTAGCCGAACACGAACTGACACTAATTGCCGATGGCACCTGCACAATCGTAATCAGTTAG | 35 | 1 |
| PA#6/49 | ATACCAGCTTATTCAATTGGAGCCGAACAACTGCTTACCCTGCGTCTTATTGTCCCGTACAATCGTAATCAGTTAG | 36 | 1 |
| PA#6/55 | ATACCAGCTTATTCAATTGGAGACGACTAGCTGCTTACGATGACTCTGTACTGTAACCACAATCGTAATCAGTTAG | 37 | 1 |
| PA#6/59 | ATACCAGCTTATTCAATTACGAACAGTAGCCGCATAAACTCTACAGATATTCTCGTTGGACAATCGTAATCAGTTAG | 38 | 1 |
| PA#6/60 | ATACCAGCTTATTCAATTACGATGTAGTCCGACTCCAACTGATGATTGTTACGCCGCCACAATCGTAATCAGTTAG | 39 | 1 |
| PA#10/64 | ATACCAGCTTATTCAATTGGACGCCGACTAACTTACGATTGCTAGATAACTGTTTCCACAATCGTAATCAGTTAG | 40 | 1 |
| PA#10/65 | ATACCAGCTTATTCAATTACCGATTTAGACGATCCATACAGTCTGATTAACGTGTTGCACAATCGTAATCAGTTAG | 41 | 1 |
| PA#10/66 | ATACCAGCTTATTCAATTACGATGCCAGCCGAAACTCAGATTACGTTCTTGACCGTGGACAATCGTAATCAGTTAG | 42 | 1 |
| PA#10/68 | ATACCAGCTTATTCAATTACGATGTAGCCGTTCCCTTTACGATGTGCACCGACTAACCACAATCGTAATCAGTTAG | 43 | 1 |
| PA#10/69 | ATACCAGCTTATTCAATTGGGTACGAGATAGCCGTCTTTCGATCTGAGTCCATTGGATACAATCGTAATCAGTTAG | 44 | 1 |
| PA#10/72 | ATACCAGCTTATTCAATTCCAACTGCACGATGTAGCCGGACCTCTAATGATTACCTGTACAATCGTAATCAGTTAG | 45 | 1 |
| PA#10/74 | ATACCAGCTTATTCAATTGTACGCCGACTGACTGAGAAATGTGCTTGAGTTCGCATCGACAATCGTAATCAGTTAG | 46 | 1 |
| PA#10/77 | ATACCAGCTTATTCAATTGGAGCCGAACTGTCTGAGTAGTGTTGACATTCTTCTACGTACAATCGTAATCAGTTAG | 47 | 1 |
| PA#10/78 | ATACCAGCTTATTCAATTACCGAGACGTGGAACCGATTGTTGCCGCACTGATTATTCCACAATCGTAATCAGTTAG | 48 | 1 |
| PA#10/79 | ATACCAGCTTATTCAATTGGAGACCACCCGAACTGACTATGTAGAATGTGTCCCACCCACAATCGTAATCAGTTAG | 49 | 1 |
| PA#10/80 | ATACCAGCTTATTCAATTGTAGCAGCGACGAACTGTTATGACATTTTTTCTTGTCCTCACACAATCGTAATCAGTTAG | 50 | 1 |
| PA#14/84 | ATACCAGCTTATTCAATTCCAATGATCGATTGTTGCCCTGATTGATGGTTGTTGTCGTACAATCGTAATCAGTTAG | 51 | 1 |
| PA#14/85 | ATACCAGCTTATTCAATTGGACGCCGACTAACTTAAGCGATTTGGCCCACTCATCTCGACAATCGTAATCAGTTAG | 52 | 1 |
| PA#14/86 | ATACCAGCTTATTCAATTGGAGACGCTAACATGATGCTACGAAGGTGTGAATCGGTGCACAATCGTAATCAGTTAG | 53 | 1 |
| PA#14/89 | ATACCAGCTTATTCAATTGGGCACCACGGGAGTCGGCCACATTTGGAGTTGTTTTTGCACAATCGTAATCAGTTAG | 54 | 1 |
| PA#14/91 | ATACCAGCTTATTCAATTGGAGTGTGGCCGCCAACTGAGCTTGTTAGTGTCCTCTTGTACAATCGTAATCAGTTAG | 55 | 1 |
| PA#14/93 | ATACCAGCTTATTCAATTGTAGACGACGACTGTACGTTGACCTGCTAACCACTTCTGGACAATCGTAATCAGTT | 56 | 1 |
| PA#14/94 | ATACCAGCTTATTCAATTGCACCAGTGGAAAGATTGTAGCCGTTCCTCCTGATTATGCACAATCGTAATCAGTTAG | 57 | 1 |
| PA#14/95 | ATACCAGCTTATTCAATTGCACGGTGGGAGATTGTAGCCCCTCTTTTTTTTGCCTGTACAATCGTAATCAGTTAG | 58 | 1 |
| PA#14/97 | ATACCAGCTTATTCAATTGTAGACGACCACCTGATTAACTTTGGCCGGGCGCTTTTGTACAATCGTAATCAGTTAG | 59 | 1 |
| PA#14/99 | ATACCAGCTTATTCAATTACGATCCTTGTAGCCCAGCGCACTGATCACGCTTGTGACCACAATCGTAATCAGTTAG | 60 | 1 |
| PA#14/100 | ATACCAGCTTATTCAATTGTAGACGACGCAATATAATGATTAGTTGGCACGACCCTGCACAATCGTAATCAGTTAG | 61 | 1 |

TABLE 2

| Symbol | Meaning |
|---|---|
| R | G or A |
| Y | T/U or C |
| M | A or C |
| K | G or T/U |
| S | G or C |
| W | A or T/U |
| B | G or C or T/U |
| D | A or G or T/U |
| D | A or C or T/U |
| V | A or G or C |

Comparative sequence analyses were performed by means of ClustalW2, a multiple sequence alignment tool (http://www.ebi.ac.uk/Tools/msa/clustalw2/).

The analysis of the secondary structure of some aptamer clones was carried out by means of the internet tool "The mfold Web Server" (http://mfold.rna.albany.edu/?q=mfold), free software for folding of nucleic acids, which is based on an energy minimization algorithm. The aptamer PA#2/8 (SEQ ID NO: 1) is striking because of its G-rich sequence, which presumes folding to a G quartet structure:

PA#2/8  AGCAACATGA<u>GGGGG</u>ATAGA<u>GGGGGT</u><u>GGG</u>TTCTCTC<u>GGG</u>CT

Figure 2:
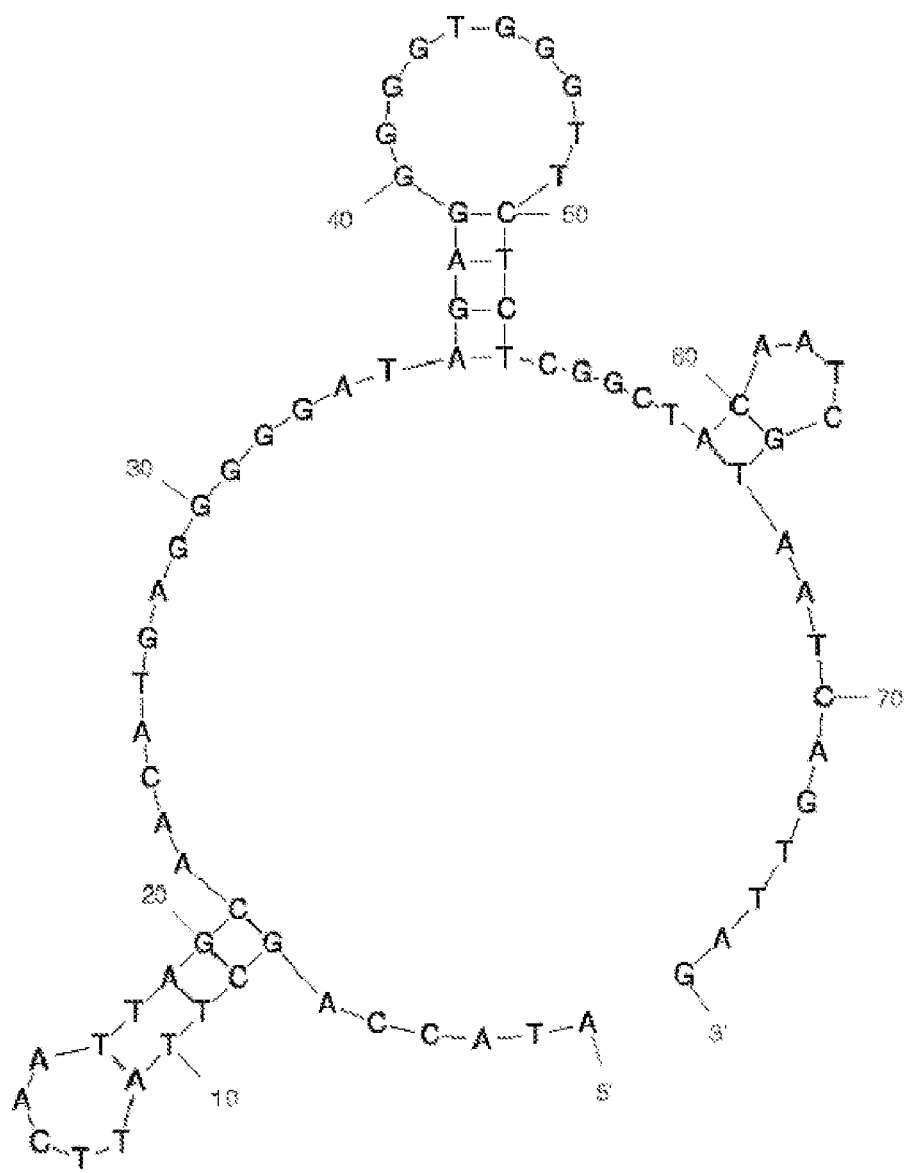
FIG. 2 depicts a possible secondary structure of aptamer PA#2/8 (SEQ ID NO: 1).

A possible secondary structure of aptamer PA#2/8 (SEQ ID NO: 1) is shown in FIG. 2.

EXAMPLE 4

Binding Tests

Aptamer clones having a different sequence are investigated for their individual binding capacity for the selection target (biotinylated protein A, immobilized on streptavidin-functionalized magnetic beads). The binding experiments are carried out under the SELEX conditions. $2.5$-$3 \times 10^7$ target-modified magnetic beads and ~55 pmol of fluorescein-labeled aptamer ssDNA in binding buffer (100 mM NaCl, 20 mM Tris-HCl, pH 7.6, 10 mM $MgCl_2$, 5 mM KCl, 1 mM $CaCl_2$) and in a binding volume of 250 µl are employed for each experiment. The target-modified magnetic beads are washed several time in binding buffer before use and the aptamer ssDNA is thermally equilibrated by incubation at 90° C. for 8 min, on ice for 10 min and at RT for ~5 min. The prepared aptamer ssDNA and the washed target-modified magnetic beads are then brought together for binding for 30 min at 21° C., while shaking. The non-bound ssDNA is removed and the binding complexes are washed several times in binding buffer. Thereafter, the target-bound ssDNA is eluted by means of heat by incubation of the binding complexes in binding buffer at 95° C. for 10 min, while shaking. This elution procedure is carried out twice in total. The amount of ssDNA eluted can be quantified on the basis of the fluorescein labeling of the aptamer ssDNA and by means of a calibration curve. This corresponds to the amount of target-bound aptamer in the binding experiment.

EXAMPLE 5

Construction of a Biosensor and Procedure for a Detection for Protein A

LIST OF REFERENCE SYMBOLS FOR FIG. 3

Figure 3:
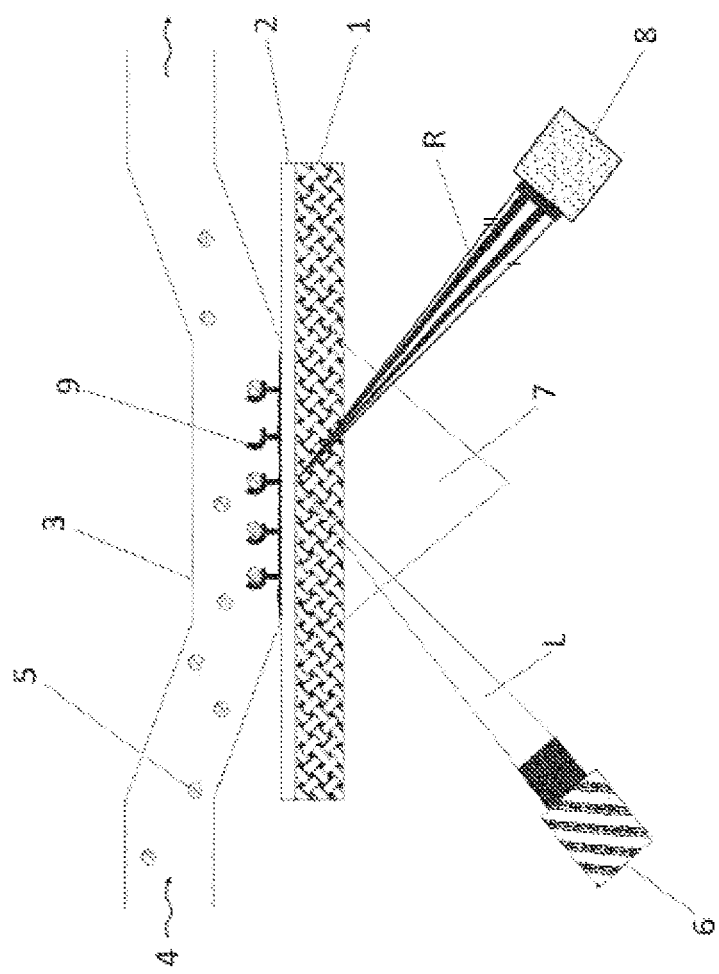
FIG. 3 depicts the use of the Biacore® system for the labeling-free detection of biomolecular interactions in real time.
Figure 4:
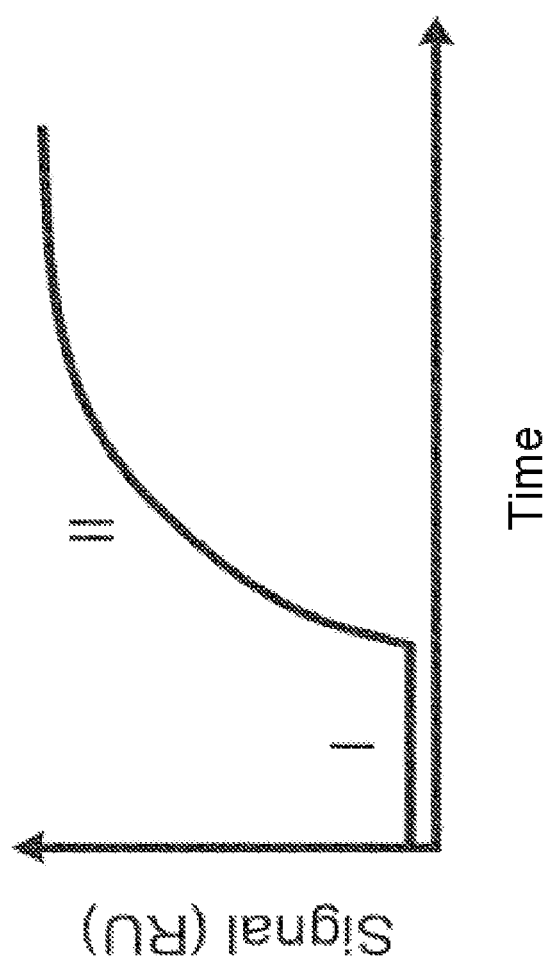
FIG. 4 is a sensorgram showing the changes in the resonance angle during binding analysis using the Biacore® system as plotted against the time.

1 Sensor chip (glass chip)
2 Gold film
3 Flow cell
4 Sample solution
5 Target
6 Light source
7 Prism
8 Detector
9 Aptamer
L Monochromatic polarized light
R Reflected light The Biacore® system is a commercially obtainable biosensor system which renders possible the labeling-free detection of biomolecular interactions in real time and utilizes for this the physical principle of surface plasmon resonance spectroscopy (SPR), as shown in FIG. 3). The biosensor chip of the Biacore system comprises a glass chip 1, which is coated with a thin gold film 2 and represents the sensor surface. A special functionalization of this sensor surface, for example with carboxymethyldextran (CM) allows covalent immobilization of the biological receptor molecules. In the case of the aptamers 9, the biotin-streptavidin coupling system is preferably utilized in order to immobilize the biotinylated aptamers on the streptavidin-coated sensor surface of the biosensor chip. The subsequent interaction between the target and aptamer takes place in a flow cell 3, wherein the sample solution 4 with the target 5 is passed over the sensor surface by an integrated, continuous flow system. The optical detection unit of the Biacore system comprises a light source 6 (light-emitting diode), a prism 7 and a detector 8 (diode array detector). Monochromatic, polarized light L is irradiated under the conditions of total reflection from a medium of high refractive index (sensor chip with gold film) into a medium of low refractive index (sensor layer, buffer solution). At a certain angle of incidence an attenuation of the reflected light R occurs here. This angle, the resonance angle, reacts very sensitively to changes in the refractive index of the sensor layer. Binding of the target 5 to the immobilized aptamer 9 on the sensor surface results in an increase in weight in the sensor layer, which leads to a change in the refractive index of this layer and therefore to a shift in the resonance angle. These changes are emitted as a measurable signal, expressed in resonance units (RU), and are proportional to the amount of target 5 bound on the sensor surface. During the binding analysis, the changes in the resonance angle are recorded continuously and plotted against the time, shown as a sensorgram, which is shown in diagram form in FIG. 4. In section II of the signal curve a shift in the resonance angle due to the binding of the target to the immobilized aptamer can be seen. The shift in the resonance angle is also shown in FIG. 3 with the aid of reflected light beam designated "I" and one designated "II".

The aptamer-target complex can be dissolved again under suitable buffer conditions, so that the sensor surface is regenerated and is available for a renewed binding with target molecules.

An aptamer according to the invention is immobilized on the surface of the biosensor described above. A solution of protein A is passed over the sensor surface, wherein protein A binds to the aptamer. The binding of protein A is detected as a shift in the resonance angle.

EXAMPLE 6

Binding Tests with Truncated Aptamers

The truncated variants of the aptamer PA#2/8 (SEQ ID NO: 1) shown in Table 3 were prepared. The aptamer PA#2/8 [A19-76] (SEQ ID NO: 69) lacks the 5' primer region and PA#2/8 [A1-58] (SEQ ID NO: 70) lacks the 3' primer region. PA#2/8CR40 (SEQ ID NO: 71) is the core region (core) without the 5' primer region and without the 3' primer region.

The binding experiments were carried out under the SELEX conditions. $2.5-3 \times 10^7$ target-modified magnetic beads and ~55 pmol of fluorescein-labeled aptamer ssDNA in binding buffer (100 mM NaCl, 20 mM Tris-HCl, pH 7.6, 10 mM $MgCl_2$, 5 mM KCl, 1 mM $CaCl_2$) were employed for each experiment. The target-modified magnetic beads were prepared as a preliminary to the binding experiments, wherein Dynabeads® M-280 Streptavidin (Invitrogen, UK) were used in order to immobilize native, biotinylated protein A from *Staphylococcus aureus* (P2165, Sigma-Aldrich, Germany). Before each binding reaction the target-modified magnetic beads were washed several times in binding buffer and the aptamer ssDNA was thermally equilibrated by incubation at 90° C. for 8 min, on ice for 10 min and then converted to RT for ~5 min. The prepared aptamer ssDNA and the washed target-modified magnetic beads were then brought together for binding and incubated for 30 min at 21° C., while shaking. The non-bound ssDNA was removed and the binding complexes were washed several times in binding buffer. Thereafter, the target-bound ssDNA was eluted by means of heat by incubation of the binding complexes in binding buffer at 95° C. for 10 min, while shaking. This elution procedure was carried out twice in total. The amount of ssDNA eluted could be quantified on the basis of the fluorescein labeling of the aptamer ssDNA and by means of a calibration curve. This corresponds to the amount of target-bound aptamer in the binding experiment.

Figure 5:
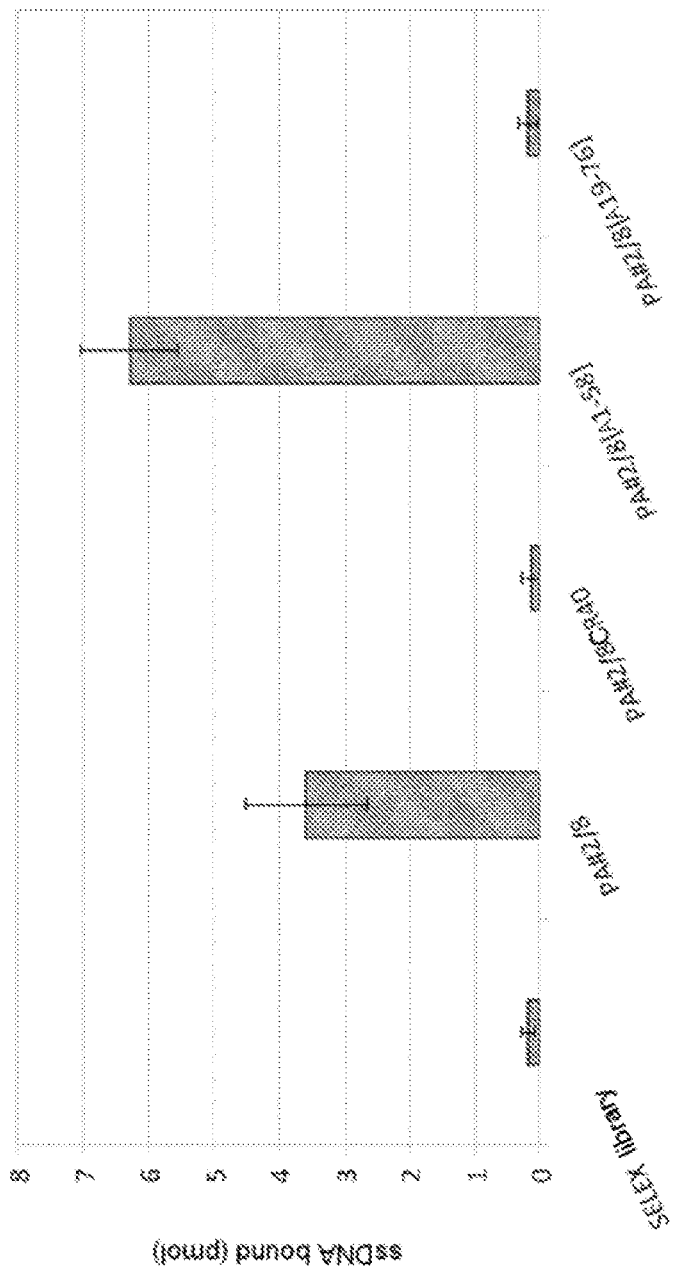
FIG. 5 shows the results of binding experiments on protein A-modified magnetic beads using the aptamer PA#2/8 and its shortened variants compared with the non-selected SELEX library as a negative control.

FIG. 5 shows the results of the bead-based binding experiments with the aptamer PA#2/8 and its shortened variants compared with the non-selected SELEX library as a negative control. The original aptamer PA#2/8 has a very good binding capacity on protein A-modified magnetic beads. After removal of the 3' primer region (variant PA#2/8 [A1-58]), this binding capacity is retained and could even be improved. The removal of the 5' primer region (variant PA#2/8 [A19-76]), on the other hand, led to a complete loss in the binding capacity of the aptamer. The same negative result was also shown by the variant without the two primer regions (PA#2/8CR40). It can so far be concluded from this that the aptamer PA#2/8 can be shortened and the core region together with the 5' primer region play an important role in the binding capacity of the aptamer.

TABLE 3

| Aptamer no. | Aptamer sequence (5' → 3') | SEQ ID NO | |
|---|---|---|---|
| PA#2/8 | ATACCAGCTTATTCAATTAGCAACAT-GAGGGGGATAGAGGGGGTGGGTTCTCTCGGCTACAATCGTAATCAGTTAG | 1 | 76nt |
| ↓ Truncated variants | | | |
| PA#2/8 [A19-76] | AGCAACATGAGGGGGATA-GAGGGGGTGGGTTCTCTCGGCTACAATCGTAATCAGTTAG | 69 | 58nt |
| PA#2/8 [A1-58] | ATACCAGCTTATTCAATTAGCAACATGAGGGGGATAGAGGGGGTGGGTTCTCTCGGCT | 70 | 58nt |
| PA#2/8CR40 | AGCAACATGAGGGGGATAGAGGGGGTGGGTTCTCTCGGCT | 71 | 40nt |

EXAMPLE 7

Labeling-Free Binding Experiments with a Biosensor

Figure 6:
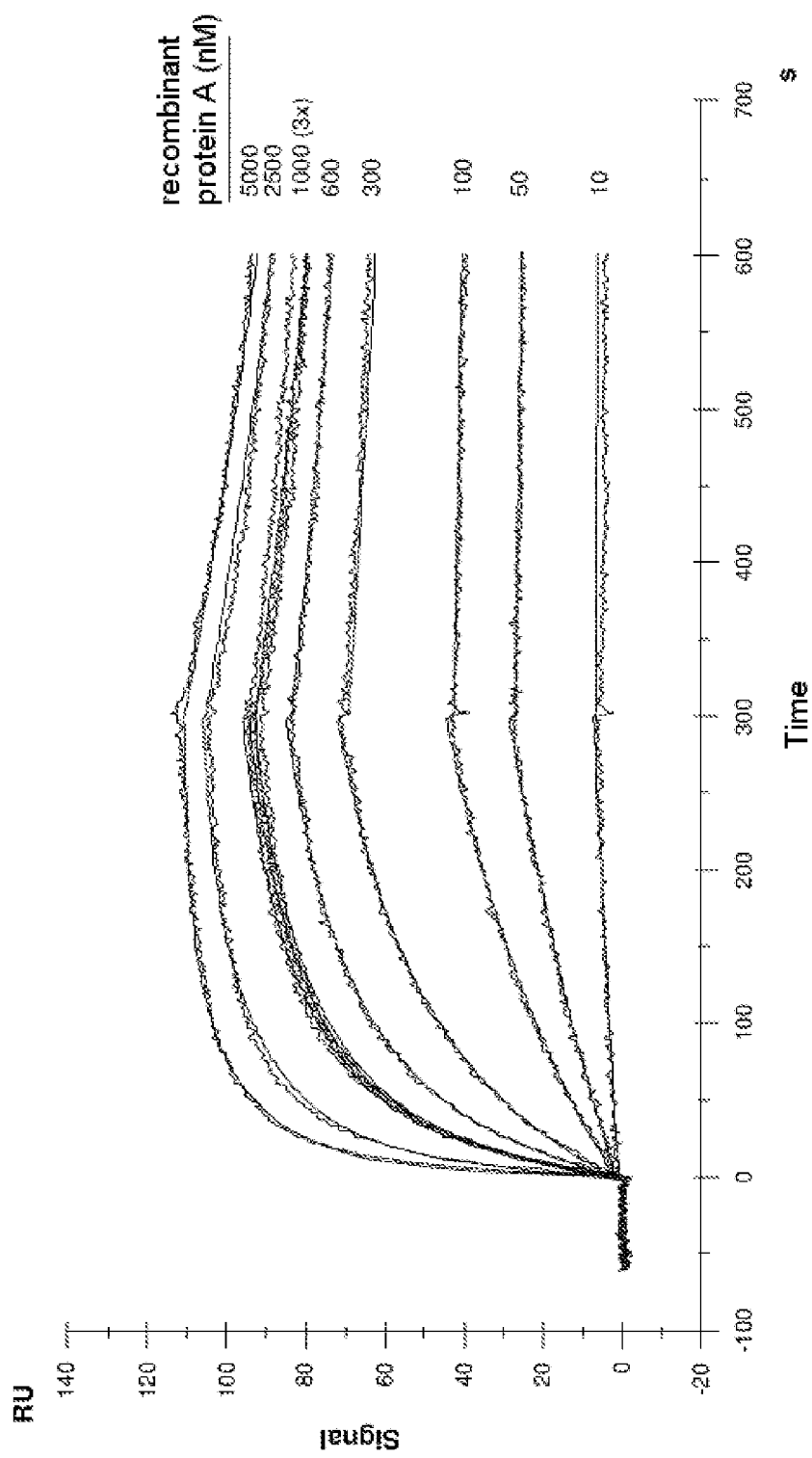
FIG. 6 is a sensorgram showing the double-referenced signal curve during the binding and dissociation phase of different concentrations of recombinant protein A with aptamer PA#2/8.

The Biacore X100 system is a commercially obtainable biosensor system (GE Healthcare, Sweden) which renders possible the labeling-free detection of biomolecular interactions in real time and utilizes for this the physical principle of surface plasmon resonance spectroscopy (SPR). For the experiments presented here, the Biotin CAPture Kit with the CAP sensor chip, which renders possible the preparation of a streptavidin-coated sensor surface, was used. The biotin-streptavidin coupling system can be utilized in this manner in order to immobilize biotinylated aptamers on the sensor surface. For the interaction analyses between the aptamer and target, the target solution is passed over the sensor surface by an integrated, continuous flow system. Binding of the target to the immobilized aptamer on the sensor surface results in an increase in weight in the sensor layer, which leads to a change in the refractive index of this layer and therefore to a shift in the resonance angle. These changes are emitted as a measurable signal, expressed in resonance units (RU), and are proportional to the amount of target bound on the sensor surface. In the experiments presented here, non-specific ssDNA (SELEX library, 3'-biotinylated) was immobilized in the reference cell and ssDNA of the aptamer PA#2/8 (3'-biotinylated) was immobilized in the measurement cell. The target solution, comprising recombinant protein A (P7837, Sigma-Aldrich, Germany) or native protein A (P3838, Sigma-Aldrich, Germany) in binding buffer (100 mM NaCl, 20 mM Tris-HCl, pH 7.6, 10 mM $MgCl_2$, 5 mM KCl, 1 mM $CaCl_2$) with 0.005% SP20, was passed over the prepared sensor surfaces at a flow rate of 10 µl/min. The interaction between the aptamer and target took place during a binding phase of 300 s, and a dissociation phase of likewise 300 s then took place. Binding buffer with 0.005% SP20 was used as the mobile buffer. The sensorgrams (FIG. 6, 8) show the double-referenced signal curve (measurement cell minus reference cell and buffer reference) during the binding and dissociation phase at different target concentrations in a range of 10 nM-5,000 nM protein A. During such a measurement series the 1,000 nM concentration of protein A was measured 3 times as a control. After each binding/dissociation the sensor surface was regenerated. The sensorgrams (FIG. 6, 8) moreover show, in addition to the experimental data, the fit of these data as an overlay. In this context it was clear that the interaction between the aptamer (ligand) and target (analyte) does not follow a 1:1 binding, but corresponds to a bivalent analyte binding. This indicates that the protein A has two or more binding sites for the aptamer.

Figure 7:
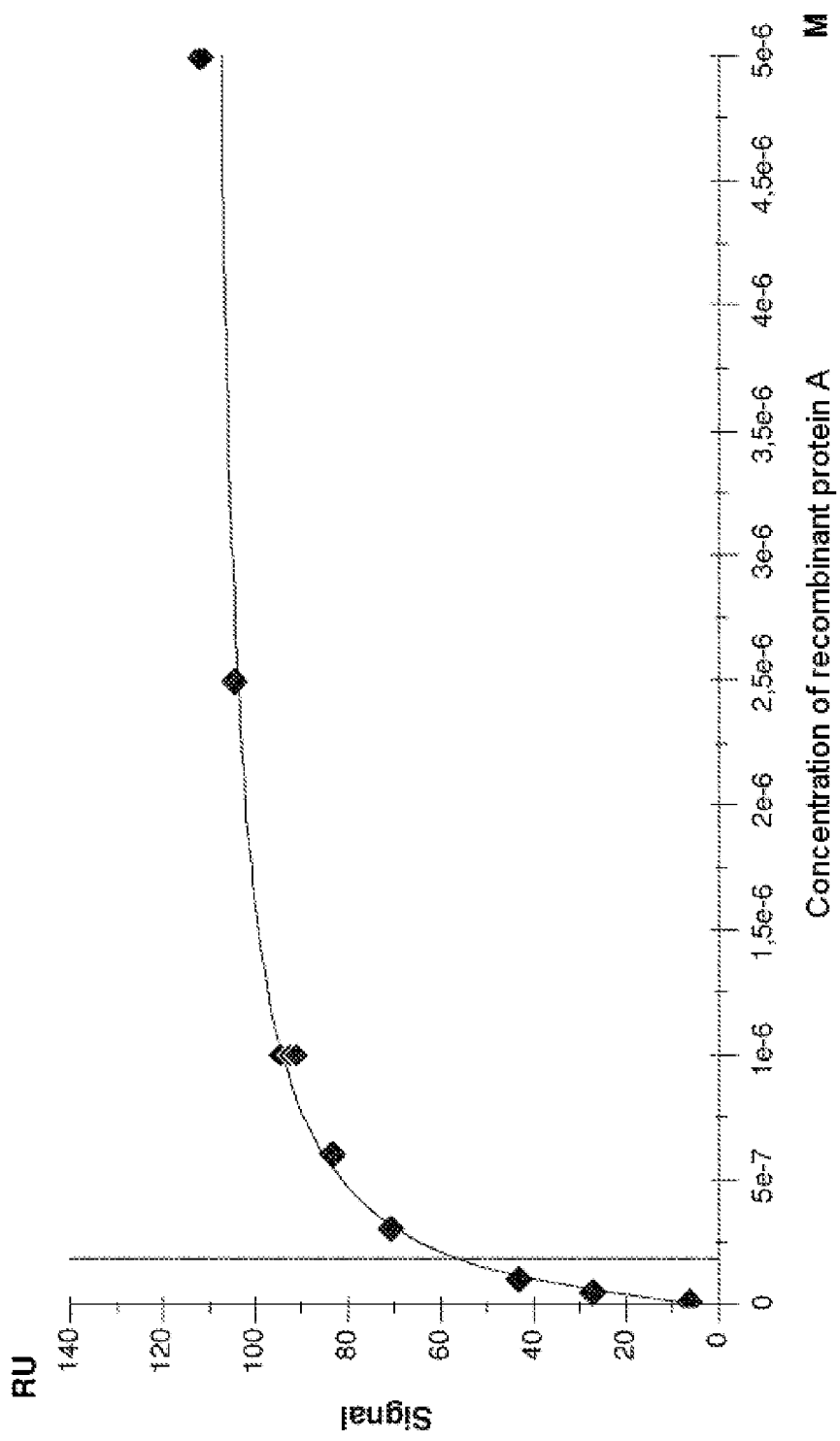
FIG. 7 depicts a saturation curve plotted from the binding data at the end of each binding phase of different concentrations of recombinant protein A with aptamer PA#2/8.
Figure 8:
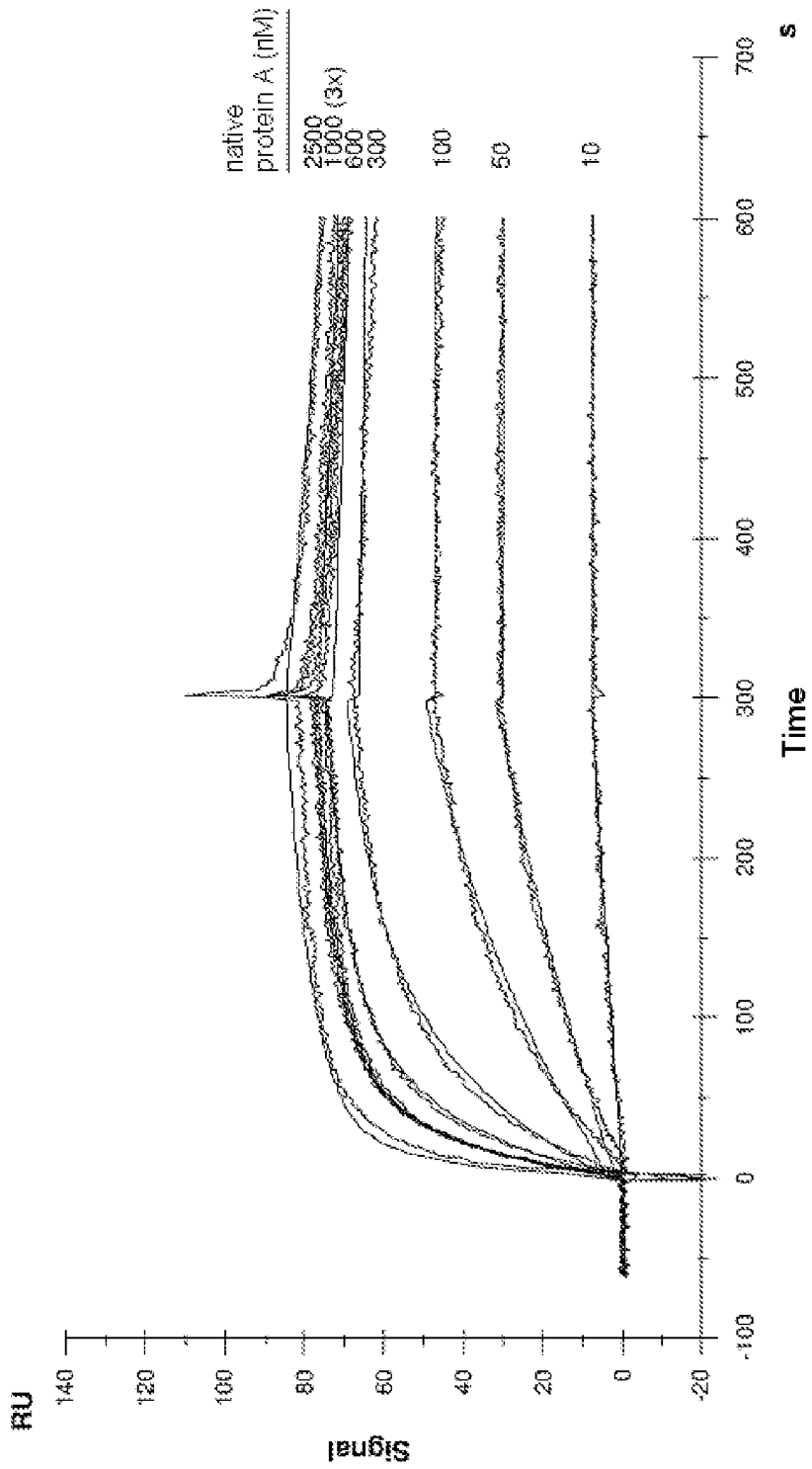
FIG. 8 is a sensorgram showing the double-referenced signal curve during the binding and dissociation phase of different concentrations of native protein A with aptamer PA#2/8.
Figure 9:
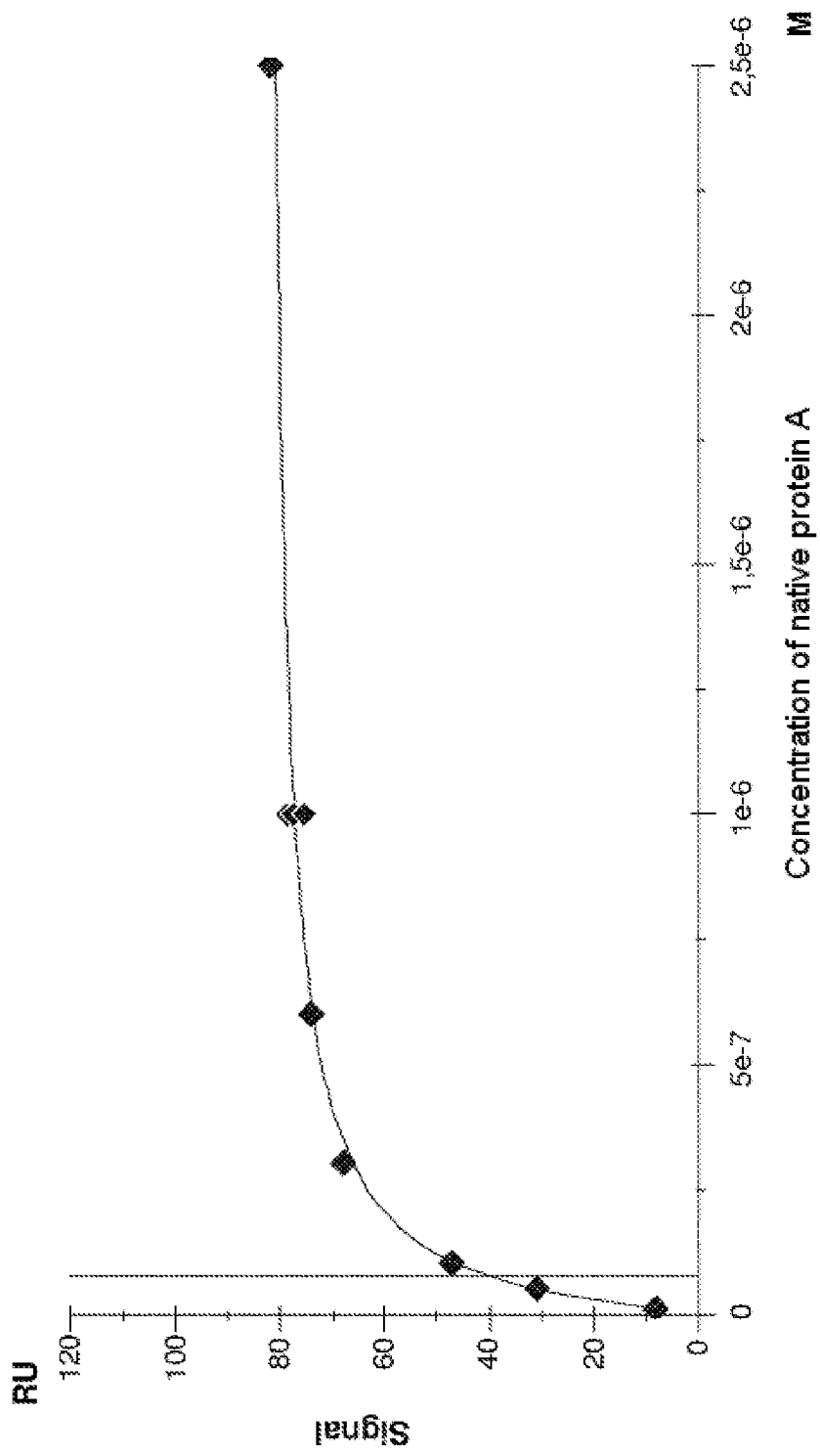
FIG. 9 depicts a saturation curve plotted from the binding data at the end of each binding phase of different concentrations of native protein A with aptamer PA#2/8.

From the binding data at the end of each binding phase with the different protein A concentrations a saturation curve was plotted (FIG. 7, 9) and the steady state affinity of the aptamer PA#2/8 for protein A was calculated from this. The calculated affinity here rather corresponds to the avidity, since in the present experimental set-up there is a bivalent binding of protein A to the immobilized aptamers. For the binding between recombinant (FIG. 6-7) or native (FIG. 8-9) protein A and the aptamer PA#2/8, an avidity of 188 nM+/−22 and, respectively, 75.3 nM+/−6.1 was determined.

The invention claimed is:

1. An aptamer comprising:
   a) a nucleic acid comprising any one of SEQ ID NOs: 1-65, with the proviso that thymine can be replaced by uracil,
   b) a nucleic acid having at least 70% sequence identity to the nucleic acid sequence of a),
   c) a nucleic acid that hybridizes with the complementary strand of the nucleic acid of a),
   d) a nucleic acid that differs from a) by one or more nucleotides that are substituted, deleted, and/or inserted, or
   e) a derivative of a), b), c), or d);
   wherein the aptamer binds to: (i) an immunoglobulin-binding cell wall protein, (ii) substances comprising an immunoglobulin-binding cell wall protein, and/or (ii) microorganisms comprising an immunoglobulin-binding cell wall protein, and
   wherein the immunoglobulin-binding cell wall protein is selected from the group consisting of protein A, G, and L.

2. A medicament comprising one or more different aptamers according to claim 1.

3. An aptamer probe for the detection of: (i) protein A, G or L, (ii) substances comprising protein A, G or L, or (iii) microorganisms comprising protein A, G or L; wherein the aptamer probe comprises one or more different aptamers according to claim 1 and a labeling agent.

4. A biosensor comprising one or more different aptamers according to claim 1.

5. A solid phase comprising one or more different immobilized aptamers of claim 1.

6. A test strip comprising one or more different aptamers of claim 1.

7. A lateral flow assay device comprising a test strip of claim 6.

8. A kit comprising one or more different aptamers according to claim 1.

9. A measuring apparatus for the detection of: (i) protein A, G or L, (ii) substances comprising protein A, G or L, or (iii) microorganisms comprising protein A, G or L; wherein the measuring apparatus comprises one or more different aptamers of claim 1.

10. A method of quantifying free binding sites on protein A, G or L, the method comprising;
    1) contacting an aptamer with: (i) a sample comprising protein A, G or L, (ii) a substance comprising protein A, G or L, or (iii) a microorganism comprising protein A, G or L; and
    2) detecting the free binding sites between the aptamer and: (i) protein A, G or L, (ii) the substance, or (ii) the microorganism;
    wherein the aptamer comprises:
    a) a nucleic acid comprising any one of SEQ ID NOs: 1-65, with the proviso that thymine can be replaced by uracil,
    b) a nucleic acid having at least 70% sequence identity to the nucleic acid sequence of a),
    c) a nucleic acid that hybridizes with the complementary strand of a nucleic acid of a),
    d) a nucleic acid that differs from a) by one or more nucleotides that are substituted, deleted, and/or inserted, or
    e) a derivative of a), b), c), or d);
    and wherein the aptamer binds to: (i) protein A, G or L, (ii) substances comprising protein A, G, or L, and/or (iii) microorganisms comprising protein A, G, or L.

11. A method of detecting protein A, G or L, substances comprising protein A, G or L, or microorganisms comprising protein A, G or L, the method comprising:

1) contacting an aptamer with a sample comprising: (i) protein A, G or L, (ii) a substance comprising protein A, G or L, or (iii) a microorganism comprising protein A, G or L; and
2) detecting the binding of the aptamer to: (i) protein A, G or L, (ii) the substance, or (iii) the microorganisms;
wherein the aptamer comprises:
a) a nucleic acid comprising any one of SEQ ID NOs: 1-65, with the proviso that thymine can be replaced by uracil,
b) a nucleic acid having at least 70% sequence identity to the nucleic acid sequence of a),
c) a nucleic acid that hybridizes with the complementary strand of a nucleic acid of a),
d) a nucleic acid that differs from a) by one or more nucleotides that are substituted, deleted, and/or inserted, or
e) a derivative of a), b), c), or d);
and wherein the aptamer binds to: (i) protein A, G, or L, (ii) substances comprising protein A, G, or L, and/or (iii) microorganisms comprising protein A, G, or L.

12. A method for enriching, separating off and/or isolating protein A, G or L, substances comprising protein A, G or L or microorganisms comprising protein A, G or L, the method comprising:
1) contacting an aptamer with a sample comprising: (i) protein A, G, or L, (ii) a substance comprising protein A, G or L and/or (iii) a microorganism comprising protein A, G, or L; wherein a complex of the aptamer and protein A, G, or L, a complex of the aptamer and the substance comprising protein A, G, or L, and/or a complex of the aptamer and the microorganism comprising protein A, G, or L is formed; and
2) separating the complex(es) from the remainder of the sample;
wherein the aptamer comprises:
a) a nucleic acid comprising any one of SEQ ID NOs: 1-65, with the proviso that thymine can be replaced by uracil,
b) a nucleic acid having at least 70% sequence identity to the nucleic acid sequence of a),
c) a nucleic acid that hybridizes with the complementary strand of a nucleic acid of a),
d) a nucleic acid that differs from a) by one or more nucleotides that are substituted, deleted, and/or inserted, or
e) a derivative of a), b), c), or d);
and wherein the aptamer binds to: (i) protein A, G or L, (ii) substances comprising protein A, G or L, and/or (iii) microorganisms comprising protein A, G, or L.

13. A method for quantifying the binding of an immunoglobulin to protein A, G, or L, the method comprising:
1) adding the immunoglobulin to: (i) protein A, G or L, (ii) a substance comprising protein A, G or L, or (iii) a microorganism comprising protein A, G or L;
2) bringing the mixture produced in 1) into contact with an aptamer; and
3) determining the amount of aptamer bound and the amount of immunoglobulin bound;
wherein the aptamer comprises:
a) a nucleic acid comprising any one of SEQ ID NOs: 1-65, with the proviso that thymine can be replaced by uracil,
b) a nucleic acid having at least 70% sequence identity to the nucleic acid sequence of a),
c) a nucleic acid that hybridizes with the complementary strand of a nucleic acid of a),
d) a nucleic acid that differs from a) by one or more nucleotides that are substituted, deleted, and/or inserted, or
e) a derivative of a), b), c), or d);
and wherein the aptamer binds to: (i) protein A, G, or L, (ii) substances comprising protein A, G, or L, and/or (iii) microorganisms comprising protein A, G, or L.

14. A measuring apparatus comprising an aptamer probe of claim 3.

15. A measuring apparatus comprising a biosensor of claim 4.

16. A measuring apparatus comprising a test strip of claim 6.

17. The aptamer probe of claim 3, wherein the microorganism is *Staphylococcus aureus, Streptococcus* or *Peptostreptococcus*.

18. The method of claim 11, wherein the microorganism is *Staphylococcus aureus, Streptococcus* or *Peptostreptococcus*.

19. The method of claim 12, wherein the microorganism is *Staphylococcus aureus, Streptococcus* or *Peptostreptococcus*.

20. The method of claim 12, further comprising isolating protein A, G or L, the substance comprising protein A, G or L, or the microorganism comprising protein A, G or L.

21. A method of blocking free binding sites on protein A, G or L, the method comprising contacting an aptamer with: (i) a sample comprising protein A, G or L, (ii) a substance comprising protein A, G or L , or (iii) a microorganism comprising protein A, G, or L;
wherein the aptamer comprises:
a) a nucleic acid comprising any one of SEQ ID NOs: 1-65, with the proviso that thymine can be replaced by uracil,
b) a nucleic acid having at least 70% sequence identity to the nucleic acid sequence of a),
c) a nucleic acid that hybridizes with the complementary strand of a nucleic acid of a),
d) a nucleic acid that differs from a) by one or more nucleotides that are substituted, deleted, and/or inserted, or
e) a derivative of a), b), c), or d); and wherein the aptamer binds to: (i) protein A, G, or L, (ii) substances comprising protein A, G, or L, and/or (iii) microorganisms comprising protein A, G, or L.

22. The method of claim 11, wherein the aptamer comprises a nucleic acid sequence that has at least 90% sequence identity to the nucleic acid sequence of a).

23. The method of claim 11, wherein the aptamer comprises a nucleic acid sequence that has at least 95% sequence identity to the nucleic acid sequence of a).

24. The aptamer of claim 1, wherein the aptamer comprises a nucleic acid comprising SEQ ID NO: 1, with the proviso that thymine can be replaced by uracil.

25. The aptamer of claim 1, wherein the aptamer comprises a nucleic acid sequence that has at least 90% sequence identity to the nucleic acid sequence of a).

26. The aptamer of claim 1, wherein the aptamer comprises a nucleic acid sequence that has at least 95% sequence identity to the nucleic acid sequence of a).

27. The aptamer of claim 1, wherein the aptamer comprises a nucleic acid that hybridizes with the complementary strand of a nucleic acid of a) and is a fragment of the nucleic acid of a), the fragment having a length of at least 40 nucleotides.

28. The aptamer of claim 1, wherein the aptamer comprises a nucleic acid that hybridizes with the complementary strand of a nucleic acid of a) and is a fragment of the nucleic acid of a), the fragment having a length of at least 30 nucleotides.

29. The aptamer of claim 1, wherein the aptamer comprises a nucleic acid that differs from a) by up to 10 nucleotides that are substituted, deleted, and/or inserted.

30. The aptamer of claim 1, wherein the aptamer comprises a nucleic acid that differs from a) by up to 5 nucleotides that are substituted, deleted, and/or inserted.

31. The aptamer of claim 1, wherein the aptamer comprises a nucleic acid comprising any one of SEQ ID NOs: 1-65 and up to 20 nucleotides at the 5' and/or at the 3' end thereof, with the proviso that thymine can be replaced by uracil.

32. The aptamer of claim 1, wherein the aptamer comprises a derivative of a), b), c), or d), wherein the derivative differs from a), b), c), or d) in that it:
   i) has, on at least one nucleotide, an alkylation, arylation, acetylation, alkoxylation, halogenation, or an amino group or another functional group;
   ii) has a base modification;
   iii) is labelled;
   iv) has a enantiomeric nucleotide;
   v) is present completely or partially as phosphorothioate RNA or DNA, phosphorodithioate RNA or DNA, phosphoroselenoate RNA or DNA, phosphorodiselenoate RNA or DNA, phosphoroamidate RNA or DNA, locked nucleic acid, peptide nucleic acid, N3'-P5' phosphoroamidate RNA or DNA, cyclohexene-nucleic acid, or tricyclo-DNA;
   vi) is a spiegelmer thereof; and/or
   vii) has phosphoroamidate-morpholine (PMO) components.

33. The aptamer of claim 1 comprising:
   a) a nucleic acid comprising SEQ ID NO: 1, with the proviso that thymine can be replaced by uracil,
   b) a nucleic acid having at least 90% sequence identity to the nucleic acid sequence of a),
   c) a fragment of SEQ ID NO: 1, the fragment having a length of at least 40 nucleotides,
   d) a nucleic acid that differs from a) by up to 5 nucleotides that are substituted, deleted, and/or inserted, or
   e) a derivative of a), b), c), or d), wherein the derivative differs from a), b), c), or d) in that it:
      i) has, on at least one nucleotide, an alkylation, arylation, acetylation, alkoxylation, halogenation, or an amino group or another functional group;
      ii) has a base modification;
      iii) is labelled;
      iv) has a enantiomeric nucleotide;
      v) is present completely or partially as phosphorothioate RNA or DNA, phosphorodithioate RNA or DNA, phosphoroselenoate RNA or DNA, phosphorodiselenoate RNA or DNA, phosphoroamidate RNA or DNA, locked nucleic acid, peptide nucleic acid, N3'-P5' phosphoroamidate RNA or DNA, cyclohexene-nucleic acid, or tricyclo-DNA;
      vi) is a spiegelmer thereof; and/or
      vii) has phosphoroamidate-morpholine (PMO) components.

34. The aptamer of claim 33 comprising a nucleic acid having at least 95% sequence identity to the nucleic acid sequence of a).

35. The aptamer of claim 1, wherein the aptamer comprises a nucleic acid comprising SEQ ID NO:1 and up to 20 nucleotides at 5' and/or at the 3' end thereof, with the proviso that thymine can be replaced by uracil.

36. A method of detecting protein A, G or L, substances comprising protein A, G or L, or microorganisms comprising protein A, G or L, the method comprising:
   1) contacting the aptamer of claim 33 with a sample comprising: (i) protein A, G or L,
      (ii) a substance comprising protein A, G, or L, or (iii) a microorganism comprising protein A, G, or L; and
   2) detecting the binding of the aptamer to: (i) protein A, G or L, (ii) the substance, or
      (iii) the microorganism.

37. The method of claim 33 wherein the aptamer comprises a nucleic acid having at least 95% sequence identity to SEQ ID NO: 1.

38. A medicament comprising the aptamer of claim 33.

39. An aptamer probe for the detection of: (i) protein A, G or L, (ii) substances comprising protein A, G or L, or (iii) microorganisms comprising protein A, G or L; wherein the aptamer probe comprises the aptamer of claim 33 and a labeling agent.

40. A biosensor comprising the aptamer of claim 33.

41. A solid phase comprising the aptamer of claim 33.

42. A test strip comprising the aptamer of claim 33.

43. A kit comprising the aptamer of claim 33.

44. A measuring apparatus for the detection of: (i) protein A, G or L, (ii) substances comprising protein A, G or L, or (iii) microorganisms comprising protein A, G or L; wherein the measuring apparatus comprises the aptamer of claim 33.

* * * * *